(12) United States Patent
Chandrasegaran et al.

(10) Patent No.: US 9,057,057 B2
(45) Date of Patent: Jun. 16, 2015

(54) OBLIGATE HETERODIMER VARIANTS OF FOKI CLEAVAGE DOMAIN

(75) Inventors: Srinivasan Chandrasegaran, Baltimore, MD (US); Sivaprakash Ramalingam, Baltimore, MD (US); Karthikeyan Kandavelou, Pondicherry (IN)

(73) Assignees: THE JOHNS HOPKINS UNIVERSITY, Baltimore, MD (US); PONDICHERRY BIOTECH PRIVATE LIMITED (PBPL), Pondicherry (IN)

( * ) Notice: Subject to any disclaimer, the term of this patent is extended or adjusted under 35 U.S.C. 154(b) by 0 days.

(21) Appl. No.: 13/812,857

(22) PCT Filed: Jul. 27, 2011

(86) PCT No.: PCT/US2011/045558
§ 371 (c)(1),
(2), (4) Date: Jan. 28, 2013

(87) PCT Pub. No.: WO2012/015938
PCT Pub. Date: Feb. 2, 2012

(65) Prior Publication Data
US 2013/0130350 A1    May 23, 2013

Related U.S. Application Data

(60) Provisional application No. 61/368,024, filed on Jul. 27, 2010.

(51) Int. Cl.
C12N 9/22      (2006.01)
C12N 15/52     (2006.01)
C12N 15/62     (2006.01)
C12N 9/16      (2006.01)
C07K 14/47     (2006.01)

(52) U.S. Cl.
CPC .............. *C12N 9/16* (2013.01); *C07K 14/4702* (2013.01); *C07K 2319/70* (2013.01)

(58) Field of Classification Search
CPC combination set(s) only.
See application file for complete search history.

(56) References Cited

U.S. PATENT DOCUMENTS

| | | | |
|---|---|---|---|
| 4,797,368 A | | 1/1989 | Carter et al. |
| 5,173,414 A | | 12/1992 | Lebkowski et al. |
| 7,888,121 B2 * | | 2/2011 | Urnov et al. ............. 435/463 |
| 8,592,645 B2 * | | 11/2013 | DeKelver et al. ......... 800/278 |
| 2005/0026157 A1 * | | 2/2005 | Baltimore et al. ........... 435/6 |
| 2005/0064474 A1 * | | 3/2005 | Urnov et al. ............... 435/6 |
| 2008/0159996 A1 | | 7/2008 | Ando et al. |
| 2009/0305346 A1 | | 12/2009 | Miller |
| 2010/0047805 A1 | | 2/2010 | Wang |
| 2010/0055793 A1 | | 3/2010 | Chandrasegaran |

FOREIGN PATENT DOCUMENTS

| WO | WO-91/16024 A1 | 10/1991 |
|---|---|---|
| WO | WO-91/17424 A1 | 11/1991 |
| WO | WO-93/24641 A2 | 12/1993 |
| WO | WO-94/26877 A1 | 11/1994 |

OTHER PUBLICATIONS

Ramalingam, S. et al., 'Creating Designed Zinc-Finger Nucleases with Minimal Cytotoxicty,' J. Mol. Biol. Epub Nov. 19, 2010, vol. 405, pp. 630-641.
Ahmad et al., Cancer Res. 52:4817-4820 (1992).
Alvarez et al., Hum. Gene Ther. 5:597-613 (1997).
Anderson, Science 256:808-813 (1992).
Behr et al., 20 Bioconjugate Chem. 5:382-389 (1994).
Beumer et al., (2006) *Genetics*. 172, 2391-2403.
Bibikova et al., (2003) *Science*. 300, 764.
Bibikova et al., (2001) Mol Cell Biol. 21, 289-297.
Bibikova, M., Golic, M., Golic, K.G. and Carroll, D. (2002) *Genetics*. 161, 1169-1175.
Bitinaite et al., (1998) *Proc. Natl. Acad. Sci. USA.* 95, 10570-10575.
Blaese et al., Cancer Gene Ther. 2:291-297 (1995).
Blaese et al., Science 270:475-480 (1995).
Buchscher et al., J. Virol. 66:2731-2739 (1992).
Catto et al., (2006) Nucleic Acids Research. 34, 1711-1720.
Crystal, Science 270:404-410 (1995).
Dillon, TIBTECH 11:167175 (1993).
Doyon et al., (2008) Nat Biotechnol. 26, 702-708.
Dranoff et al., Hum. Gene Ther. 1:111-2 (1997).
Dull et al. (1998) J. Virol. 72:8463-8471.
Dunbar et al., Blood 85:3048-305 (1995).
Durai et al., (2006) J. of Combinatorial Chemistry & High Throughput Screening. 9, 301-311.
Durai et al., (2005) 20 Nucleic Acids Research. 33, 5978-5990.
Ellem et al., Immunol Immunother. 44(1):10-20 (1997).
Fields et al. (1989) Nature 340:245-246.
Foley et al., (2009) PLoS ONE. 4, e4348.
Follenzi et al. (2000) Nature Genetics 25:217-222.
Gao et al., Gene Therapy 2:710-722 (1995).
Geurts, A.M., Cost, G.J., Freyvert, Y., Zeitler, B., Miller, J.C., et al. (2009) Science. 325, 433.
Gribskov, Nucl. Acids Res. 14(6):6745-6763 (1986).
Haddada et al., in Current Topics in Microbiology and Immunology Doerfler and Bohm (eds.) (1995).
Han et al., Proc. Natl. Acad. Sci. USA 92:9747-9751 (1995).
Hermonat & Muzyczka, PNAS 81:6466-6470 (1984).
Hockemeyer et al., Genetic engineering of human pluripotent cells using TALE nucleases, Nat Biotechnol. Jul 7, 2011. doi: 10.1038/nbt.1927.

(Continued)

*Primary Examiner* — Kagnew H Gebreyesus
(74) *Attorney, Agent, or Firm* — Venable LLP; Stefan J. Kirchanski

(57) ABSTRACT

Disclosed are methods of making and using engineered FokI cleavage domain variants. Also disclosed are methods, compositions and fusion proteins containing obligate heterodimers of engineered FokI cleavage domain variants and DNA binding domains, such as zinc finger protein (ZFP) domains and transcription activator-like effector (TALE) domains.

6 Claims, 13 Drawing Sheets

(56) References Cited

OTHER PUBLICATIONS

Hockemeyer et al., (2009) Nat Biotechnol 27, 851-857.
Inaba et al., J. Exp. Med. 176:1693-1702 (1992).
Johann et al., J. Virol. 66:1635-1640 (1992).
Kandavelou et al., (2005) Nat Biotechnol. 23, 686-687.
Kandavelou et al., (2009). Biochein BiophyRes Commun. 388, 56-61.
Kearns et al., Gene Ther. 9:748-55-1996 (Abstract Only).
Kim, H.J., Lee, H.J., Kim, H., Cho, S.W. and Kim, J.S. (2009) Genome Res. 19, 1279-1288.
Kim, Y-G., and Chandrasegaran, S. (1994). Proc. Natl. Acad.Sci. USA. 91, 883-887.
Kim et al., (1996) Proc. Natl. Acad. Sci USA. 93, 11565 1160.
Kohn et al., Nat. Med. 1:1017-102 (1995).
Kotin, Human Gene Therapy 5:793-801 (1994).
Kremer & Perricaudet, British Medical Bulletin 51(1):31-44 (1995).
Li, L., Wu, L.P., and Chandrasegaran, S. (1992). Proc. Natl. Acad. Sci. USA. 89, 4275-4279.
Lin, L. and Chandrasegaran, S. (1993) Proc. Natl. Acad. Sci. USA. 90, 2764-2768.
Lombardo et al., (2007) Nat Biotechnol 25, 1298-1306.
Maeder et al., (2008) Mol Cell. 31, 25 294-301.
Malech et al., PNAS 94:22 12133-12138 (1997).
Mani et al., (2005) Biochem Biophys Res Conznzun. 335, 447-457.
Mani et al., (2005) Biochem Biophyl Res Commun. 334, 1191-1197.
Mashimo et al., (2010) PLoS ONE. 5, e8870.
Meng et al., (2008) Nat Biotechnol. 26, 695-701.
Miller et al., A TALE nuclease architecture for efficient genome editing, Nat Biotechnol. Feb. 2011;29(2):143-8.
Miller et al., J. Virol. 65:2220-2224 (1991.
Miller et al., (2007) Nat Biotechnol. 25, 778-785.
Miller, Nature 357:455-460 (1992).
Mitani & Caskey, TIBTECH 11:162-166 (1993).
Morton et al., (2006) Proc Natl Acad Sci. USA. 103, 16370-16375.
Muzyczka, J. Clin. Invest. 94:1351 (1994).
Nabel & Feigner, TIBTECH 11:211-217 (1993).
Ni et al. (2005) "Evaluation of biodistribution and safety of adenovirus vectors containing group B fibers after intravenous injection into baboons," Hum Gene Ther 16:664-677.

Nilsson et al. (2004) "Development of an adenoviral vector system with adenovirus serotype 35 tropism; efficient transient gene transfer into primary malignant hematopoietic cells," J Gene Med 6:631-641.
Naldini et al. (1996) Proc. Natl. Acad. Sci. USA 93:11382-11388.
Perez et al., (2008) Nat Biotechnol. 26, 808-816.
Porteus, M.H. and Baltimore, D. (2003) Science. 300, 763.
Pruett-Miller et al., (2008) Molecular Therapy ,16, 707-717.
Pruett-Miller et al., (2009) PLoS Genet. 5, e1000376.
Remy et al., Bioconjugate Chem. 5:647-654 (1994).
Rosenecker et al., Infection 24:1 5-10 (1996).
Samulski et al., J. Virol. 63:03822-3828 (1989).
Schroers et al. (2004) "Gene transfer into human T lymphocytes and natural killer cells by; Ad5/F35 chimeric adenoviral vectors," Exp Hematol 32:536-546.
Seshidhar et al. (2003) "Development of adenovirus serotype 35 as a gene transfer vector," Virology 311:384-393.
Shayakhmetov et al. (2000) "Efficient gene transfer into human CD34(+) cells by a retargeted adenovirus vector," J Virol 74:2567-2583.
Shukla et al., (2009) Nature. 459, 437-441.
Smith and Waterman, Advances in Applied Mathematics 2:482-489 (1981).
Smith et al., (2000) Nucleic Acids Res. 28, 3361-3369.
Sommerfelt et al., Virol. 176:58-59 (1990).
Soya et al. (2004), "A tumor-targeted and conditionally replicating oncolytic adenovirus vector expressing TRAIL for treatment of liver metastases," Mol Ther 9:496-509.
Sterman et al., Hum. Gene Ther. 7:1083-1089 (1998).
Szczepek et al., (2007) Nat Biotechnol, 25, 786-793.
Topf et al., Gene Ther. 5:507-513 (1998).
Townsend et al., (2009) Nature. 459, 442-445.
Tratschin, et al., Mol. Cell. Biol. 4:2072-2081 (1984).
Urnov et al., (2005) Nature. 435, 646-651.
Vanamee et al., (2001)1 Mol. Biol. 309, 69-78.
Lisovoski, Restorative Neurology and Neuroscience 8:45-46 (1995).
Wagner et al., Lancet 351:9117 1702-3 (1998).
Wah et al., (1998) Proc Natl Acad Sci USA 95:10564-10569.
Welsh et al., Hum. Gene Ther. 2:205-18 (1995).
West et al., Virology 160:38-47 (1987).
Wilson et al., J. Virol. 63:2374-2378 (1989).
Wu et al., (2007) Cellular and Molecular Life Sciences. 64, 2933-2944.
Yu et al., Gene Therapy 1:13-26 (1994).
Zuffery et al. (1998) J. Virol. 72:9873-9880.

\* cited by examiner

FokI nuclease domain mutant REL (PBPL/JHU)
D483R:Q486E:I499L (REL)

Protein Sequence:
QLVKSELEEKKSELRHKLKYVPHEYIELIEIARNSTQDRILEMKVMEFFMKVYGYRGKHLGG
SRKPDGAIYTVGSPIDYGVIVDTKAYSGGYNLPIGQAREMERYVEENQTRNKHLNPNEWWK
VYPSSVTEFKFLFVSGHFKGNYKAQLTRLNHITNCNGAVLSVEELLIGGEMIKAGTLTLEEVR
RKFNNGEINF (SEQ ID NO: 1)

DNA Sequence:
CAACTAGTCAAAAGTGAACTGGAGGAGAAGAAATCTGAACTTCGTCATAAATTGAAATA
TGTGCCTCATGAATATATTGAATTAATTGAAATTGCCAGAAATTCCACTCAGGATAGAAT
TCTTGAAATGAAGGTAATGGAATTTTTTATGAAAGTTTATGGATATAGAGGTAAACATTT
GGGTGGATCAAGGAAACCGGACGGAGCAATTTATACTGTCGGATCTCCTATTGATTACG
GTGTGATCGTGGATACTAAAGCTTATAGCGGAGGTTATAATCTGCCAATTGGCCAAGCAC
GTGAAATGGAACGATATGTCGAAGAAAATCAAACACGAAACAAACATCTCAACCCTAAT
GAATGGTGGAAAGTCTATCCATCTTCTGTAACGGAATTTAAGTTTTTATTTGTGAGTGGT
CACTTTAAAGGAAACTACAAAGCTCAGCTTACACGATTAAATCATATCACTAATTGTAAT
GGAGCTGTTCTTAGTGTAGAAGAGCTTTTAATTGGTGGAGAAATGATTAAAGCCGGCAC
ATTAACCTTAGAGGAAGTGAGACGGAAATTTAATAACGGCGAGATAAACTTTTAA (SEQ
ID NO: 2)

FIGURE 1

FokI nuclease domain mutant DKK (PBPL/JHU)
R487D:E490K:I538K

Protein Sequence:
QLVKSELEEKKSELRHKLKYVPHEYIELIEIARNSTQDRILEMKVMEFFMKVYGYRGKHLGG
SRKPDGAIYTVGSPIDYGVIVDTKAYSGGYNLPIGQADEMQDYVKENQTRNKHINPNEWWK
VYPSSVTEFKFLFVSGHFKGNYKAQLTRLNHKTNCNGAVLSVEELLIGGEMIKAGTLTLEEV
RRKFNNGEINF (SEQ ID NO: 3)

DNA Sequence:
CAACTAGTCAAAAGTGAACTGGAGGAGAAGAAATCTGAACTTCGTCATAAATTGAAATA
TGTGCCTCATGAATATATTGAATTAATTGAAATTGCCAGAAATTCCACTCAGGATAGAAT
TCTTGAAATGAAGGTAATGGAATTTTTTATGAAAGTTTATGGATATAGAGGTAAACATTT
GGGTGGATCAAGGAAACCGGACGGAGCAATTTATACTGTCGGATCTCCTATTGATTACG
GTGTGATCGTGGATACTAAAGCTTATAGCGGAGGTTATAATCTGCCAATTGGCCAAGCA
GATGAAATGCAAGATTATGTCAAAGAAAATCAAACACGAAACAAACATATCAACCCTAA
TGAATGGTGGAAAGTCTATCCATCTTCTGTAACGGAATTTAAGTTTTTATTTGTGAGTGGT
CACTTTAAAGGAAACTACAAAGCTCAGCTTACACGATTAAATCATAAAACTAATTGTAAT
GGAGCTGTTCTTAGTGTAGAAGAGCTTTTAATTGGTGGAGAAATGATTAAAGCCGGCAC
ATTAACCTTAGAGGAAGTGAGACGGAAATTTAATAACGGCGAGATAAACTTTTAA (SEQ
ID NO: 4)

FIGURE 2

FokI nuclease domain mutant RVEL (PBPL/JHU)
D483R:Q486E:I499L:I538V

Protein Sequence:
QLVKSELEEKKSELRHKLKYVPHEYIELIEIARNSTQDRILEMKVMEFFMKVYGYRGKHL
GGSRKPDGAIYTVGSPIDYGVIVDTKAYSGGYNLPIGQAREMERYVEENQTRNKHLNPN
EWWKVYPSSVTEFKFLFVSGHFKGNYKAQLTRLNHVTNCNGAVLSVEELLIGGEMIKA
GTLTLEEVRRKFNNGEINF (SEQ ID NO: 5)

DNA Sequence:
CAACTAGTCAAAAGTGAACTGGAGGAGAAGAAATCTGAACTTCGTCATAAATTGAA
ATATGTGCCTCATGAATATATTGAATTAATTGAAATTGCCAGAAATTCCACTCAGGA
TAGAATTCTTGAAATGAAGGTAATGGAATTTTTTATGAAAGTTTATGGATATAGAGG
TAAACATTTGGGTGGATCAAGGAAACCGGACGGAGCAATTTATACTGTCGGATCTCC
TATTGATTACGGTGTGATCGTGGATACTAAAGCTTATAGCGGAGGTTATAATCTGCC
AATTGGCCAAGCACGTGAAATGGAACGATATGTCGAAGAAAATCAAACACGAAACA
AACATCTCAACCCTAATGAATGGTGGAAAGTCTATCCATCTTCTGTAACGGAATTTA
AGTTTTTATTTGTGAGTGGTCACTTTAAAGGAAACTACAAAGCTCAGCTTACACGATT
AAATCATgTCACTAATTGTAATGGAGCTGTTCTTAGTGTAGAAGAGCTTTTAATTGGT
GGAGAAATGATTAAAGCCGGCACATTAACCTTAGAGGAAGTGAGACGGAAATTTAA
TAACGGCGAGATAAACTTTTAA (SEQ ID NO: 6)

FIGURE 3

FokI nuclease domain mutant DKAK (PBPL/JHU)
R487D:E490K:I499A:I538K

Protein Sequence:
QLVKSELEEKKSELRHKLKYVPHEYIELIEIARNSTQDRILEMKVMEFFMKVYGYRGKHL
GGSRKPDGAIYTVGSPIDYGVIVDTKAYSGGYNLPIGQAADEMQDYVKENQTRNKHAN
PNEWWKVYPSSVTEFKFLFVSGHFKGNYKAQLTRLNHKTNCNGAVLSVEELLIGGEMIK
AGTLTLEEVRRKFNNGEINF (SEQ ID NO: 7)

DNA Sequence:
CAACTAGTCAAAAGTGAACTGGAGGAGAAGAAATCTGAACTTCGTCATAAATTGAA
ATATGTGCCTCATGAATATATTGAATTAATTGAAATTGCCAGAAATTCCACTCAGGA
TAGAATTCTTGAAATGAAGGTAATGGAATTTTTTATGAAAGTTTATGGATATAGAGG
TAAACATTTGGGTGGATCAAGGAAACCGGACGGAGCAATTTATACTGTCGGATCTCC
TATTGATTACGGTGTGATCGTGGATACTAAAGCTTATAGCGGAGGTTATAATCTGCC
AATTGGCCAAGCAGATGAAATGCAAGATTATGTCAAAGAAAATCAAACACGAAACA
AACATGCCAACCCTAATGAATGGTGGAAAGTCTATCCATCTTCTGTAACGGAATTTA
AGTTTTTATTTGTGAGTGGTCACTTTAAAGGAAACTACAAAGCTCAGCTTACACGATT
AAATCATAAAACTAATTGTAATGGAGCTGTTCTTAGTGTAGAAGAGCTTTTAATTGGT
GGAGAAATGATTAAAGCCGGCACATTAACCTTAGAGGAAGTGAGACGGAAATTTAA
TAACGGCGAGATAAACTTTTAA (SEQ ID NO: 8)

FIGURE 4

FokI nuclease domain variant with StsI segment containing REL mutations (PBPL/JHU)

Protein Sequence:
QLVKSELEEKKSELRHKLKYVPHEYIELIEIARNSTQDRILEMKVMEFFMKVYGYRGKHL
GGSRKPDGAIYTVGSPIDYGVILDSKAYSEGFPLTASHTRAMERYLRQFTERKEELKPTW
WDIAPEHLDNTYFAYVSGSFSGNYKEQLQKFRQDTNCNGAVLSVEELLIGGEMIKAGTL
TLEEVRRKFNNGEINF (SEQ ID NO: 9)

DNA Sequence:
GGACTAGTCAAAAGTGAACTGGAGGAGAAGAAATCTGAACTTCGTCATAAATTGAA
ATATGTGCCTCATGAATATATTGAATTAATTGAAATTGCCAGAAATTCCACTCAGGA
TAGAATTCTTGAAATGAAGGTAATGGAATTTTTTATGAAAGTTTATGGATATAGAGG
TAAACATTTGGGTGGATCAAGGAAACCGGACGGAGCAATTTATACTGTCGGATCTCC
TATTgattgtgcaattattcttgattcaaaagcttactcagaaggcttccactcactgcctcccacacacgagctatggaaagat
atttgaggcaatttacagagcgaaaagaagaactcaagccaacgtggtgggatattgctccagaacatttagacaatacatatttc
gcttacgtttctgggagttttcgggtaattataaggaacagttacaaaaatttaggcaagatACTAATTGTAATGGAGC
TGTTCTTAGTGTAGAAGAGCTTTTAATTGGTGGAGAAATGATTAAAGCCGGCACATT
AACCTTAGAGGAAGTGAGACGGAAATTTAATAACGGCGAGATAAACTTTTAA (SEQ
ID NO: 10)

FIGURE 5

FokI nuclease domain variant with StsI segment containing DKK mutations (PBPL/JHU)

Protein Sequence:
QLVKSELEEKKSELRHKLKYVPHEYIELIEIARNSTQDRILEMKVMEFFMKVYGYRGKHL
GGSRKPDGAIYTVGSPIDYGVILDSKAYSEGFPLTASHTDAMGDYLKQFTERKEEIKPTW
WDIAPEHLDNTYFAYVSGSFSGNYKEQLQKFRQKTNCNGAVLSVEELLIGGEMIKAGTL
TLEEVRRKFNNGEINF (SEQ ID NO: 11)

*Helices α4 and α5 are highlighted/double underlined; StsI segment incorporated into FokI nuclease domain is shown in underline.

DNA Sequence:
GGACTAGTCAAAAGTGAACTGGAGGAGAAGAAATCTGAACTTCGTCATAAATTGAA
ATATGTGCCTCATGAATATATTGAATTAATTGAAATTGCCAGAAATTCCACTCAGGA
TAGAATTCTTGAAATGAAGGTAATGGAATTTTTTATGAAAGTTTATGGATATAGAGG
TAAACATTTGGGTGGATCAAGGAAACCGGACGGAGCAATTTATACTGTCGGATCTCC
TATTgattgtgcaattattcttgattcaaaagcttactcagaaggcttccactcactgcctcccacacagatgctatgggagattatttgaaac
aatttacagagcgaaaagaagaaataaagccaacgtggtgggatattgctccagaacatttagacaatacatatttcgcttacgtttctggggagt
ttttcgggtaattataaggaacagttacaaaaatttaggcaaaaaACTAATTGTAATGGAGCTGTTCTTAGTGTAG
AAGAGCTTTTAATTGGTGGAGAAATGATTAAAGCCGGCACATTAACCTTAGAGGAAG
TGAGACGGAAATTTAATAACGGCGAGATAAACTTTTAA (SEQ ID NO: 12)

FIGURE 6

FokI wild-type nuclease domain

Protein Sequence:
QLVKSELEEKKSELRHKLKYVPHEYIELIEIARNSTQDRILEMKVMEFFMKVYGYRGKHL
GGSRKPDGAIYTVGSPIDYGVIVDTKAYSGGYNLPIGQADEMQRYVEENQTRNKHINPN
EWWKVYPSSVTEFKFLFVSGHFKGNYKAQLTRLNHITNCNGAVLSVEELLIGGEMIKAG
TLTLEEVRRKFNNGEINF (SEQ ID NO: 13)

DNA Sequence:
CAACTAGTCAAAAGTGAACTGGAGGAGAAGAAATCTGAACTTCGTCATAAATTGAA
ATATGTGCCTCATGAATATATTGAATTAATTGAAATTGCCAGAAATTCCACTCAGGA
TAGAATTCTTGAAATGAAGGTAATGGAATTTTTTATGAAAGTTTATGGATATAGAGG
TAAACATTTGGGTGGATCAAGGAAACCGGACGGAGCAATTTATACTGTCGGATCTCC
TATTGATTACGGTGTGATCGTGGATACTAAAGCTTATAGCGGAGGTTATAATCTGCC
AATTGGCCAAGCAGATGAAATGCAACGATATGTCGAAGAAAATCAAACACGAAACA
AACATATCAACCCTAATGAATGGTGGAAAGTCTATCCATCTTCTGTAACGGAATTTA
AGTTTTTATTTGTGAGTGGTCACTTTAAAGGAAACTACAAAGCTCAGCTTACACGATT
AAATCATATCACTAATTGTAATGGAGCTGTTCTTAGTGTAGAAGAGCTTTTAATTGGT
GGAGAAATGATTAAAGCCGGCACATTAACCTTAGAGGAAGTGAGACGGAAATTTAA
TAACGGCGAGATAAACTTTTAA (SEQ ID NO: 14)

FIGURE 7

FokI nuclease domain mutant DA (Cathoman Lab)

Protein Sequence:
QLVKSELEEKKSELRHKLKYVPHEYIELIEIARNSTQDRILEMKVMEFFMKVYGYRGKHL
GGSRKPDGAIYTVGSPIDYGVIVDTKAYSGGYNLPIGAADEMQDYVEENQTRNKHINPN
EWWKVYPSSVTEFKFLFVSGHFKGNYKAQLTRLNHITNCNGAVLSVEELLIGGEMIKAG
TLTLEEVRRKFNNGEINF (SEQ ID NO: 15)

DNA Sequence:
CAACTAGTCAAAAGTGAACTGGAGGAGAAGAAATCTGAACTTCGTCATAAATTGAA
ATATGTGCCTCATGAATATATTGAATTAATTGAAATTGCCAGAAATTCCACTCAGGA
TAGAATTCTTGAAATGAAGGTAATGGAATTTTTTATGAAAGTTTATGGATATAGAGG
TAAACATTTGGGTGGATCAAGGAAACCGGACGGAGCAATTTATACTGTCGGATCTCC
TATTGATTACGGTGTGATCGTGGATACTAAAGCTTATAGCGGAGGTTATAATCTGCC
AATTGGCCAAGCAGATGAAATGCAAGATTATGTCGAAGAAAATCAAACACGAAACA
AACATGCCAACCCTAATGAATGGTGGAAAGTCTATCCATCTTCTGTAACGGAATTTA
AGTTTTTATTTGTGAGTGGTCACTTTAAAGGAAACTACAAAGCTCAGCTTACACGATT
AAATCATATCACTAATTGTAATGGAGCTGTTCTTAGTGTAGAAGAGCTTTTAATTGGT
GGAGAAATGATTAAAGCCGGCACATTAACCTTAGAGGAAGTGAGACGGAAATTTAA
TAACGGCGAGATAAACTTTTAA (SEQ ID NO: 16)

FIGURE 8

FokI nuclease domain mutant RV (Cathoman Lab)

Protein Sequence:
QLVKSELEEKKSELRHKLKYVPHEYIELIEIARNSTQDRILEMKVMEFFMKVYGYRGKHL
GGSRKPDGAIYTVGSPIDYGVIVDTKAYSGGYNLPIGQA<u>R</u>EMQRYVEENQTRNKHINPN
EWWKVYPSSVTEFKFLFVSGHFKGNYKAQLTRLNH<u>V</u>TNCNGAVLSVEELLIGGEMIKA
GTLTLEEVRRKFNNGEINF (SEQ ID NO: 17)

DNA Sequence:
CAACTAGTCAAAAGTGAACTGGAGGAGAAGAAATCTGAACTTCGTCATAAATTGAA
ATATGTGCCTCATGAATATATTGAATTAATTGAAATTGCCAGAAATTCCACTCAGGA
TAGAATTCTTGAAATGAAGGTAATGGAATTTTTTATGAAAGTTTATGGATATAGAGG
TAAACATTTGGGTGGATCAAGGAAACCGGACGGAGCAATTTATACTGTCGGATCTCC
TATTGATTACGGTGTGATCGTGGATACTAAAGCTTATAGCGGAGGTTATAATCTGCC
AATTGGCCAAGCACGTGAAATGCAACGATATGTCGAAGAAAATCAAACACGAAACA
AACATATCAACCCTAATGAATGGTGGAAAGTCTATCCATCTTCTGTAACGGAATTTA
AGTTTTTATTTGTGAGTGGTCACTTTAAAGGAAACTACAAAGCTCAGCTTACACGATT
AAATCATGTCACTAATTGTAATGGAGCTGTTCTTAGTGTAGAAGAGCTTTTAATTGGT
GGAGAAATGATTAAAGCCGGCACATTAACCTTAGAGGAAGTGAGACGGAAATTTAA
TAACGGCGAGATAAACTTTTAA (SEQ ID NO: 18)

FIGURE 9

FokI nuclease domain mutant EL (Sangamo)

Protein Sequence:
QLVKSELEEKKSELRHKLKYVPHEYIELIEIARNSTQDRILEMKVMEFFMKVYGY
RGKHLGGSRKPDGAIYTVGSPIDYGVIVDTKAYSGGYNLPIGQADEM<u>E</u>RYVEEN
QTRNKH<u>L</u>NPNEWWKVYPSSVTEFKFLFVSGHFKGNYKAQLTRLNHITNCNGAV
LSVEELLIGGEMIKAGTLTLEEVRRKFNNGEINF (SEQ ID NO: 19)

DNA Sequence:
CAACTAGTCAAAAGTGAACTGGAGGAGAAGAAATCTGAACTTCGTCATAAATTGAA
ATATGTGCCTCATGAATATATTGAATTAATTGAAATTGCCAGAAATTCCACTCAGGA
TAGAATTCTTGAAATGAAGGTAATGGAATTTTTTATGAAAGTTTATGGATATAGAGG
TAAACATTTGGGTGGATCAAGGAAACCGGACGGAGCAATTTATACTGTCGGATCTCC
TATTGATTACGGTGTGATCGTGGATACTAAAGCTTATAGCGGAGGTTATAATCTGCC
AATTGGCCAAGCAGATGAAATGGAACGATATGTCGAAGAAAATCAAACACGAAACA
AACATCTCAACCCTAATGAATGGTGGAAAGTCTATCCATCTTCTGTAACGGAATTTA
AGTTTTTATTTGTGAGTGGTCACTTTAAAGGAAACTACAAAGCTCAGCTTACACGATT
AAATCATATCACTAATTGTAATGGAGCTGTTCTTAGTGTAGAAGAGCTTTTAATTGGT
GGAGAAATGATTAAAGCCGGCACATTAACCTTAGAGGAAGTGAGACGGAAATTTAA
TAACGGCGAGATAAACTTTTAA (SEQ ID NO: 20)

FIGURE 10

FokI nuclease domain mutant KK(Sangamo)

Protein Sequence:
QLVKSELEEKKSELRHKLKYVPHEYIELIEIARNSTQDRILEMKVMEFFMKVYGYRGKHL
GGSRKPDGAIYTVGSPIDYGVIVDTKAYSGGYNLPIGQADEMQRYVKENQTRNKHINPN
EWWKVYPSSVTEFKFLFVSGHFKGNYKAQLTRLNHKTNCNGAVLSVEELLIGGEMIKA
GTLTLEEVRRKFNNGEINF (SEQ ID NO: 21)

DNA Sequence:
CAACTAGTCAAAAGTGAACTGGAGGAGAAGAAATCTGAACTTCGTCATAAATTGAA
ATATGTGCCTCATGAATATATTGAATTAATTGAAATTGCCAGAAATTCCACTCAGGA
TAGAATTCTTGAAATGAAGGTAATGGAATTTTTTATGAAAGTTTATGGATATAGAGG
TAAACATTTGGGTGGATCAAGGAAACCGGACGGAGCAATTTATACTGTCGGATCTCC
TATTGATTACGGTGTGATCGTGGATACTAAAGCTTATAGCGGAGGTTATAATCTGCC
AATTGGCCAAGCAGATGAAATGCAACGATATGTCAAAGAAAATCAAACACGAAACA
AACATATCAACCCTAATGAATGGTGGAAAGTCTATCCATCTTCTGTAACGGAATTTA
AGTTTTTATTTGTGAGTGGTCACTTTAAAGGAAACTACAAAGCTCAGCTTACACGATT
AAATCATAAAACTAATTGTAATGGAGCTGTTCTTAGTGTAGAAGAGCTTTTAATTGGT
GGAGAAATGATTAAAGCCGGCACATTAACCTTAGAGGAAGTGAGACGGAAATTTAA
TAACGGCGAGATAAACTTTTAA (SEQ ID NO: 22)

FIGURE 11

α4 and α5 Helices

Protein Sequence:
IVDTKAYSGGYNLP*IGQADEMQRYVE*ENQTRNKHINPNEWWKVYPSSVTEFKFLF
VSGHFKG*NYKAQLTRLNHIT*N (SEQ ID NO: 23)

FIGURE 12

FIGURE 14 (A) and (B)

FIGURE 14 (C) and (D)

| | |
|---|---|
| Transduced mutant eGFP locus | BstXI          CCR5 sequence          BstXI<br>......CTACCCATAATAATGGACTGTCCCCTTCTGGGCTCACTATGCTGCCGCCCAGCCATGATGATGGAAGCAG......<br>(SEQ ID NO: 24) |
| Endogenous CCR5 locus near the 3-finger ZFN sites* |                ZFN-L           ZFN-R<br>TTTTTCCTTCTTACTGTCCCCTTCTGGGCTCACTATGCTGCCGCCCAGTGGGACTTTGGAAATACA WT<br>(SEQ ID NO: 25)<br>TTTTTCCTTCTTACTGTCCCCTTCTGGGCTCACTATatGCTGCCGCCCAGTGGGACTTTGGAAATA GFP⁻1(2)ᵗ<br>TTTTTCCTTCTTACTGTCCCCTTCTGGGC.......GCTGCCGCCCAGTGGGACTTTGGAAATACA GFP⁺1(2)<br>(SEQ ID NO: 26 and SEQ ID NO: 27)<br>TTTTTCCTTCTTACTGTCCCCTTCTGGGCgggcTCACTATGCTGCCGCCCAGTGGGACTTTGGAAA GFP⁺2(2)<br>TTTTTCCTTCTTACTGTCCCCTTCTGGGCTCACTATgctGCTGCCGCCCAGTGGGACTTTGGAAAT GFP⁺2(2)<br>(SEQ ID NO: 28 and SEQ ID NO: 29)<br>TTTTTCCTTCTTACTGTCCCCTTC....CTCACTATGCTGCCGCCCAGTGGGACTTTGGAAATACA GFP⁺3(1)<br>TTTTTCCTTCTTACTGTCCCCTTC.......CTATGCTGCCGCCCAGTGGGACTTTGGAAATACA GFP⁺3(3)<br>(SEQ ID NO: 30 and SEQ ID NO: 31)<br>TTTTTCCTTCTTACTGTCCCCTTC............CTGCCGCCCAGTGGGACTTTGGAAATACA GFP⁺4(1)<br>TTTTTCCTTCTTACTGTCCCCTTCTGGGCTCAtcaCTATGCTGCCGCCCAGTGGGACTTTGGAAAT GFP⁺4(3)<br>(SEQ ID NO: 32 and SEQ ID NO: 33)<br>TTTTTCCTTCTTACTGTCCCCTTCTGGGCTCACTATtatGCTGCCGCCCAGTGGGACTTTGGAAAT GFP⁺5(2)^<br>TTTTTCCTTCTTACTGTCCCCTTCTGGGCTCACTATtatGCTGCCGCCCAGTGGGACTTTGGAAAT GFP⁺5(2)<br>(SEQ ID NO: 34and SEQ ID NO: 35)<br>TTTTTCCTTCTTACTGTCCCCTTCTGGGCT.......CTGCCGCCCAGTGGGACTTTGGAAATACA GFP⁺6(3)<br>TTTTTCCTTCTTACTGTCCCCTTCTGGGCtctCACTATGCTGCCGCCCAGTGGGACTTTGGAAATA GFP⁻6(1)<br>(SEQ ID NO: 36 and SEQ ID NO: 37)<br>TTTTTCCTTCTTACTGTCCCCTTCTGG........TGCTGCCGCCCAGTGGGACTTTGGAAATACA GFP⁺7(2)<br>TTTTTCCTTCTTACTGTCCCCTTCTGGGCTCAC...GCTGCCGCCCAGTGGGACTTTGGAAATACA GFP⁺7(2)<br>(SEQ ID NO: 38 and SEQ ID NO: 39)<br>TTTTTCCTTCTTACTGTCCCCTTCTGGGCTCA.......GCCGCCCAGTGGGACTTTGGAAATACA GFP⁻8(1)<br>TTTTTCCTTCTTACTGTCCCCTTC.............TGCCGCCCAGTGGGACTTTGGAAATACA GFP⁺8(3)<br>(SEQ ID NO: 40 and SEQ ID NO: 41)<br>TTTTTCCTTCTTACTGTCCCCTTCTGGGCtcactTCACTATGCTGCCGCCCAGTGGGACTTTGGAA GFP⁺9(3)<br>TTTTTCCTTCTTACTGTCCCCTTCTGGG..........TGCCGCCCAGTGGGACTTTGGAAATACA GFP⁺9(1)<br>(SEQ ID NO: 42 and SEQ ID NO: 43) |
| Transduced mutant eGFP locus | BstXI          CCR5 sequence          BstXI<br>CAGCCGCTACCCATAATAATGGGTCATCCTCATCCTGATAAACTGCAAAAGCCATGATGATGGAAGCAGCACGA<br>(SEQ ID NO: 44) |
| Endogenous CCR5 locus near the 4-finger ZFN sites* |              ZFN-L          ZFN-R<br>GGGCAACATGCTGGTCATCCTCATCCTGATAAACTGCAAAAGGCTGAAGAGCATGACTGACATCTA WT<br>(SEQ ID NO: 45)<br>GGGCAACATGCTGGTCATCCTCATCC.....AACTGCAAAAGGCTGAAGAGCATGACTGACATCTA GFP⁺1(2)<br>GGGCAACATGCTGGTCATCCTCATCCTGATaaAAACTGCAAAAGGCTGAAGAGCATGACTGACATC GFP⁺1(2)<br>(SEQ ID NO: 46 and SEQ ID NO: 47)<br>GGGCAACATGCTGGTCATCCTCAT.......ACTGCAAAAGGCTGAAGAGCATGACTGACATCTA GFP⁺2(3)<br>GGGCAACATGCTGGTCATCCTCATCCT...AACTGCAAAAGGCTGAAGAGCATGACTGACATCTA GFP⁺2(1)<br>(SEQ ID NO: 48 and SEQ ID NO: 49)<br>GGGCAACATGCTGGTCATCCTCATCCTgatGATAAACTGCAAAAGGCTGAAGAGCATGACTGACAT GFP⁺3(3)<br>GGGCAACATGCTGGTCATCCTCATCCTGAT....AAAAGCTGAAGAGCATGACTGACATCTA GFP⁺3(1)<br>(SEQ ID NO: 50 and SEQ ID NO: 51) |

FIGURE 15

SEQUENCE LISTING

```
<160> NUMBER OF SEQ ID NOS: 69

<210> SEQ ID NO 1
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Arg Glu Met Glu Arg Tyr Val Glu Glu Asn Gln Thr Arg
            100                 105                 110

Asn Lys His Leu Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 2
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 2

```
caactagtca aaagtgaact ggaggagaag aaatctgaac ttcgtcataa attgaaatat    60
gtgcctcatg aatatattga attaattgaa attgccagaa attccactca ggatagaatt   120
cttgaaatga aggtaatgga atttttttatg aaagtttatg gatatagagg taaacatttg   180
ggtggatcaa ggaaaccgga cggagcaatt tatactgtcg gatctcctat tgattacggt   240
gtgatcgtgg atactaaagc ttatagcgga ggttataatc tgccaattgg ccaagcacgt   300
gaaatggaac gatatgtcga agaaaatcaa acacgaaaca acatctcaa ccctaatgaa    360
tggtggaaag tctatccatc ttctgtaacg gaatttaagt ttttatttgt gagtggtcac   420
tttaaaggaa actacaaagc tcagcttaca cgattaaatc atatcactaa ttgtaatgga   480
gctgttctta gtgtagaaga gcttttaatt ggtggagaaa tgattaaagc cggcacatta   540
accttagagg aagtgagacg gaaatttaat aacggcgaga taaactttta a             591
```

<210> SEQ ID NO 3
<211> LENGTH: 196
<212> TYPE: PRT
<213> ORGANISM: Artificial Sequence
<220> FEATURE:
<223> OTHER INFORMATION: Description of Artificial Sequence: Synthetic
  polypeptide

<400> SEQUENCE: 3

```
Gln Leu Val Lys Ser Glu Leu Glu Glu Lys Lys Ser Glu Leu Arg His
1               5                   10                  15
Lys Leu Lys Tyr Val Pro His Glu Tyr Ile Glu Leu Ile Glu Ile Ala
            20                  25                  30
Arg Asn Ser Thr Gln Asp Arg Ile Leu Glu Met Lys Val Met Glu Phe
        35                  40                  45
Phe Met Lys Val Tyr Gly Tyr Arg Gly Lys His Leu Gly Gly Ser Arg
    50                  55                  60
Lys Pro Asp Gly Ala Ile Tyr Thr Val Gly Ser Pro Ile Asp Tyr Gly
65                  70                  75                  80
Val Ile Val Asp Thr Lys Ala Tyr Ser Gly Gly Tyr Asn Leu Pro Ile
                85                  90                  95
Gly Gln Ala Asp Glu Met Gln Asp Tyr Val Lys Glu Asn Gln Thr Arg
            100                 105                 110
Asn Lys His Ile Asn Pro Asn Glu Trp Trp Lys Val Tyr Pro Ser Ser
        115                 120                 125
Val Thr Glu Phe Lys Phe Leu Phe Val Ser Gly His Phe Lys Gly Asn
    130                 135                 140
Tyr Lys Ala Gln Leu Thr Arg Leu Asn His Lys Thr Asn Cys Asn Gly
145                 150                 155                 160
Ala Val Leu Ser Val Glu Glu Leu Leu Ile Gly Gly Glu Met Ile Lys
                165                 170                 175
Ala Gly Thr Leu Thr Leu Glu Glu Val Arg Arg Lys Phe Asn Asn Gly
            180                 185                 190
Glu Ile Asn Phe
        195
```

<210> SEQ ID NO 4
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
caactagtca aaagtgaact ggaggagaag aaatctgaac ttcgtcataa attgaaatat      60
gtgcctcatg aatatattga attaattgaa attgccagaa attccactca ggatagaatt     120
cttgaaatga aggtaatgga attttttatg aaagtttatg gatatagagg taaacatttg     180
ggtggatcaa ggaaaccgga cggagcaatt tatactgtcg gatctcctat tgattacggt     240
gtgatcgtgg atactaaagc ttatagcgga ggttataatc tgccaattgg ccaagcagat     300
gaaatgcaag attatgtcaa agaaaatcaa acacgaaaca acatatcaa ccctaatgaa      360 tggtggaaag tctatccatc ttctgtaacg gaatttaagt ttttatttgt gagtggtcac     420
tttaaaggaa actacaaagc tcagcttaca cgattaaatc ataaaactaa ttgtaatgga     480
gctgttctta gtgtagaaga cttttaatt ggtggagaaa tgattaaagc cggcacatta      540
accttagagg aagtgagacg gaaatttaat aacggcgaga taaacttta a               591

<210> SEQ ID NO 5
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Arg Glu Met Glu Arg Tyr Val Glu Glu Asn Gln Thr Arg
            100                 105                 110

Asn Lys His Leu Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Val Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195

<210> SEQ ID NO 6
<211> LENGTH: 591

-continued

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
caactagtca aaagtgaact ggaggagaag aaatctgaac ttcgtcataa attgaaatat     60
gtgcctcatg aatatattga attaattgaa attgccagaa attccactca ggatagaatt    120
cttgaaatga aggtaatgga attttttatg aaagtttatg gatatagagg taaacatttg    180
ggtggatcaa ggaaaccgga cggagcaatt tatactgtcg gatctcctat tgattacggt    240
gtgatcgtgg atactaaagc ttatagcgga ggttataatc tgccaattgg ccaagcacgt    300
gaaatggaac gatatgtcga agaaaatcaa acacgaaaca acatctcaa ccctaatgaa     360
tggtggaaag tctatccatc ttctgtaacg gaatttaagt tttatttgt gagtggtcac     420
tttaaaggaa actacaaagc tcagcttaca cgattaaatc atgtcactaa ttgtaatgga    480
gctgttctta gtgtagaaga cttttaatt ggtggagaaa tgattaaagc cggcacatta     540
accttagagg aagtgagacg gaaatttaat aacggcgaga taaactttta a             591

<210> SEQ ID NO 7
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Tyr Asn Leu Pro Ile
                85                  90                  95

Gly Gln Ala Ala Asp Glu Met Gln Asp Tyr Val Lys Glu Asn Gln Thr
            100                 105                 110

Arg Asn Lys His Ala Asn Pro Asn Glu Trp Trp Lys Val Tyr Pro Ser
        115                 120                 125

Ser Val Thr Glu Phe Lys Phe Leu Phe Val Ser Gly His Phe Lys Gly
    130                 135                 140

Asn Tyr Lys Ala Gln Leu Thr Arg Leu Asn His Lys Thr Asn Cys Asn
145                 150                 155                 160

Gly Ala Val Leu Ser Val Glu Glu Leu Leu Ile Gly Gly Met Ile
                165                 170                 175

Lys Ala Gly Thr Leu Thr Leu Glu Glu Val Arg Arg Lys Phe Asn Asn
            180                 185                 190

Gly Glu Ile Asn Phe
        195

<210> SEQ ID NO 8
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
caactagtca aaagtgaact ggaggagaag aaatctgaac ttcgtcataa attgaaatat      60
gtgcctcatg aatatattga attaattgaa attgccagaa attccactca ggatagaatt     120
cttgaaatga aggtaatgga attttttatg aaagtttatg gatatagagg taaacatttg     180
ggtggatcaa ggaaaccgga cggagcaatt tatactgtcg gatctcctat tgattacggt     240
gtgatcgtgg atactaaagc ttatagcgga ggttataatc tgccaattgg ccaagcagat     300
gaaatgcaag attatgtcaa agaaaatcaa acacgaaaca acatgccaa ccctaatgaa      360
tggtggaaag tctatccatc ttctgtaacg gaatttaagt ttttatttgt gagtggtcac     420
tttaaaggaa actacaaagc tcagcttaca cgattaaatc ataaaactaa ttgtaatgga     480
gctgttctta gtgtagaaga gcttttaatt ggtggagaaa tgattaaagc cggcacatta     540
acttagagg aagtgagacg gaaatttaat aacggcgaga taaacttta a               591
```

<210> SEQ ID NO 9
<211> LENGTH: 195
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
        50                  55                  60

Lys Pro Asp Gly Ala Ile Tyr Thr Val Gly Ser Pro Ile Asp Tyr Gly
65                  70                  75                  80

Val Ile Leu Asp Ser Lys Ala Tyr Ser Glu Gly Phe Pro Leu Thr Ala
                85                  90                  95

Ser His Thr Arg Ala Met Glu Arg Tyr Leu Arg Gln Phe Thr Glu Arg
            100                 105                 110

Lys Glu Glu Leu Lys Pro Thr Trp Trp Asp Ile Ala Pro Glu His Leu
        115                 120                 125

Asp Asn Thr Tyr Phe Ala Tyr Val Ser Gly Ser Phe Ser Gly Asn Tyr
    130                 135                 140

Lys Glu Gln Leu Gln Lys Phe Arg Gln Asp Thr Asn Cys Asn Gly Ala
145                 150                 155                 160

Val Leu Ser Val Glu Glu Leu Leu Ile Gly Gly Glu Met Ile Lys Ala
                165                 170                 175

Gly Thr Leu Thr Leu Glu Glu Val Arg Arg Lys Phe Asn Asn Gly Glu
            180                 185                 190

Ile Asn Phe
        195

```
<210> SEQ ID NO 10
<211> LENGTH: 588
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
ggactagtca aaagtgaact ggaggagaag aaatctgaac ttcgtcataa attgaaatat    60
gtgcctcatg aatatattga attaattgaa attgccagaa attccactca ggatagaatt   120
cttgaaatga aggtaatgga attttttatg aaagtttatg gatatagagg taaacatttg   180
ggtggatcaa ggaaaccgga cggagcaatt tatactgtcg gatctcctat tgattgtgca   240
attattcttg attcaaaagc ttactcagaa ggctttccac tcactgcctc ccacacacga   300
gctatggaaa gatatttgag caatttaca gagcgaaaag aagaactcaa gccaacgtgg    360
tgggatattg ctccagaaca tttagacaat acatatttcg cttacgtttc tgggagtttt   420
tcgggtaatt ataaggaaca gttacaaaaa tttaggcaag atactaattg taatggagct   480
gttcttagtg tagaagagct tttaattggt ggagaaatga ttaaagccgg cacattaacc   540
ttagaggaag tgagacggaa atttaataac ggcgagataa acttttaa               588

<210> SEQ ID NO 11
<211> LENGTH: 195
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Leu Val Lys Ser Glu Leu Glu Lys Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
        50                  55                  60

Lys Pro Asp Gly Ala Ile Tyr Thr Val Gly Ser Pro Ile Asp Tyr Gly
65                  70                  75                  80

Val Ile Leu Asp Ser Lys Ala Tyr Ser Glu Gly Phe Pro Leu Thr Ala
                85                  90                  95

Ser His Thr Asp Ala Met Gly Asp Tyr Leu Lys Gln Phe Thr Glu Arg
            100                 105                 110

Lys Glu Glu Ile Lys Pro Thr Trp Trp Asp Ile Ala Pro Glu His Leu
        115                 120                 125

Asp Asn Thr Tyr Phe Ala Tyr Val Ser Gly Ser Phe Ser Gly Asn Tyr
    130                 135                 140

Lys Glu Gln Leu Gln Lys Phe Arg Gln Lys Thr Asn Cys Asn Gly Ala
145                 150                 155                 160

Val Leu Ser Val Glu Glu Leu Leu Ile Gly Gly Glu Met Ile Lys Ala
                165                 170                 175

Gly Thr Leu Thr Leu Glu Glu Val Arg Arg Lys Phe Asn Asn Gly Glu
            180                 185                 190
```

```
Ile Asn Phe
        195
```

<210> SEQ ID NO 12
<211> LENGTH: 588
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
ggactagtca aaagtgaact ggaggagaag aaatctgaac ttcgtcataa attgaaatat    60
gtgcctcatg aatatattga attaattgaa attgccagaa attccactca ggatagaatt   120
cttgaaatga aggtaatgga atttttttatg aaagtttatg gatatagagg taaacatttg   180
ggtggatcaa ggaaaccgga cggagcaatt tatactgtcg gatctcctat tgattgtgca   240
attattcttg attcaaaagc ttactcagaa ggctttccac tcactgcctc ccacacagat   300
gctatgggag attatttgaa acaatttaca gagcgaaaag aagaaataaa gccaacgtgg   360
tgggatattg ctccagaaca tttagacaat acatatttcg cttacgtttc tgggagtttt   420
tcgggtaatt ataaggaaca gttacaaaaa tttaggcaaa aaactaattg taatggagct   480
gttcttagtg tagaagagct tttaattggt ggagaaatga ttaaagccgg cacattaacc   540
ttagaggaag tgagacggaa atttaataac ggcgagataa acttttaa              588
```

<210> SEQ ID NO 13
<211> LENGTH: 196
<212> TYPE: PRT
<213> ORGANISM: Unknown
<220> FEATURE:
<223> OTHER INFORMATION: Description of Unknown: Wild-type
      FokI polypeptide

<400> SEQUENCE: 13

```
Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
```

Glu Ile Asn Phe
        195

<210> SEQ ID NO 14
<211> LENGTH: 591
<212> TYPE: DNA
<213> ORGANISM: Unknown
<220> FEATURE:
<223> OTHER INFORMATION: Description of Unknown: Wild-type
      FokI polynucleotide

<400> SEQUENCE: 14
caactagtca aaagtgaact ggaggagaag aaatctgaac ttcgtcataa attgaaatat      60
gtgcctcatg aatatattga attaattgaa attgccagaa attccactca ggatagaatt     120
cttgaaatga aggtaatgga atttttatg aaagtttatg gatatagagg taaacatttg      180
ggtggatcaa ggaaaccgga cggagcaatt tatactgtcg gatctcctat tgattacggt     240
gtgatcgtgg atactaaagc ttatagcgga ggttataatc tgccaattgg ccaagcagat     300
gaaatgcaac gatatgtcga agaaaatcaa acacgaaaca acatatcaa ccctaatgaa       360
tggtggaaag tctatccatc ttctgtaacg gaatttaagt tttatttgt gagtggtcac       420
tttaaaggaa actacaaagc tcagcttaca cgattaaatc atatcactaa ttgtaatgga     480
gctgttctta gtgtagaaga gctttttaatt ggtggagaaa tgattaaagc cggcacatta    540
accttagagg aagtgagacg gaaatttaat aacggcgaga taaacttta a               591

<210> SEQ ID NO 15
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
        50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Ala Ala Asp Glu Met Gln Asp Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 16
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
caactagtca aaagtgaact ggaggagaag aaatctgaac ttcgtcataa attgaaatat      60
gtgcctcatg aatatattga attaattgaa attgccagaa attccactca ggatagaatt     120
cttgaaatga aggtaatgga attttttatg aaagtttatg gatatagagg taaacatttg     180
ggtggatcaa ggaaaccgga cggagcaatt tatactgtcg gatctcctat tgattacggt     240
gtgatcgtgg atactaaagc ttatagcgga ggttataatc tgccaattgg ccaagcagat     300
gaaatgcaag attatgtcga agaaaatcaa acacgaaaca acatgccaa ccctaatgaa      360 tggtggaaag tctatccatc ttctgtaacg gaatttaagt ttttatttgt gagtggtcac     420
tttaaaggaa actacaaagc tcagcttaca cgattaaatc atatcactaa ttgtaatgga     480
gctgttctta gtgtagaaga gcttttaatt ggtggagaaa tgattaaagc cggcacatta     540
accttagagg aagtgagacg gaaatttaat aacggcgaga taaactttta a               591

<210> SEQ ID NO 17
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Leu Val Lys Ser Glu Leu Glu Glu Lys Ser Glu Leu Arg His
1               5                  10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Arg Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Val Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 18
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
caactagtca aaagtgaact ggaggagaag aaatctgaac ttcgtcataa attgaaatat      60
gtgcctcatg aatatattga attaattgaa attgccagaa attccactca ggatagaatt    120
cttgaaatga aggtaatgga attttttatg aaagtttatg gatatagagg taaacatttg    180
ggtggatcaa ggaaaccgga cggagcaatt tatactgtcg gatctcctat tgattacggt    240
gtgatcgtgg atactaaagc ttatagcgga ggttataatc tgccaattgg ccaagcacgt    300
gaaatgcaac gatatgtcga agaaaatcaa acacgaaaca acatatcaa ccctaatgaa     360 tggtggaaag tctatccatc ttctgtaacg gaatttaagt tttatttgt gagtggtcac    420 tttaaaggaa actacaaagc tcagcttaca cgattaaatc atgtcactaa ttgtaatgga    480
gctgttctta gtgtagaaga ctttttaatt ggtggagaaa tgattaaagc cggcacatta    540
accttagagg aagtgagacg gaaatttaat aacggcgaga taaacttta a              591

<210> SEQ ID NO 19
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
        50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
            100                 105                 110

Asn Lys His Leu Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly

```
                  145                 150                 155                 160
Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 20
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
caactagtca aaagtgaact ggaggagaag aaatctgaac ttcgtcataa attgaaatat        60
gtgcctcatg aatatattga attaattgaa attgccagaa attccactca ggatagaatt       120
cttgaaatga aggtaatgga atttttatg aaagtttatg gatatagagg taaacatttg        180
ggtggatcaa ggaaaccgga cggagcaatt tatactgtcg gatctcctat tgattacggt       240
gtgatcgtgg atactaaagc ttatagcgga ggttataatc tgccaattgg ccaagcagat       300
gaaatggaac gatatgtcga gaaaatcaa acacgaaaca acatctcaa ccctaatgaa         360 tggtggaaag tctatccatc ttctgtaacg gaatttaagt ttttatttgt gagtggtcac       420
tttaaaggaa actacaaagc tcagcttaca cgattaaatc atatcactaa ttgtaatgga       480
gctgttctta gtgtagaaga gcttttaatt ggtggagaaa tgattaaagc cggcacatta       540
accttagagg aagtgagacg gaaatttaat aacggcgaga taaactttta a                591

<210> SEQ ID NO 21
<211> LENGTH: 196
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140
```

```
Tyr Lys Ala Gln Leu Thr Arg Leu Asn His Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 22
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
caactagtca aaagtgaact ggaggagaag aaatctgaac ttcgtcataa attgaaatat      60
gtgcctcatg aatatattga attaattgaa attgccagaa attccactca ggatagaatt     120
cttgaaatga aggtaatgga atttttatg aaagtttatg gatatagagg taaacatttg     180
ggtggatcaa ggaaaccgga cggagcaatt tatactgtcg atctcctat tgattacggt     240 gtgatcgtgg atactaaagc ttatagcgga ggttataatc tgccaattgg ccaagcagat    300
gaaatgcaac gatatgtcaa agaaaatcaa acacgaaaca acatatcaa ccctaatgaa     360 tggtggaaag tctatccatc ttctgtaacg gaatttaagt ttttatttgt gagtggtcac    420
tttaaaggaa actacaaagc tcagcttaca cgattaaatc ataaaactaa ttgtaatgga    480
gctgttctta gtgtagaaga cttttaatt ggtggagaaa tgattaaagc cggcacatta    540
accttagagg aagtgagacg gaaatttaat aacggcgaga taaacttta a              591

<210> SEQ ID NO 23
<211> LENGTH: 76
<212> TYPE: PRT
<213> ORGANISM: Unknown
<220> FEATURE:
<223> OTHER INFORMATION: Description of Unknown: Wild-type
      FokI polypeptide

<400> SEQUENCE: 23

Ile Val Asp Thr Lys Ala Tyr Ser Gly Gly Tyr Asn Leu Pro Ile Gly
1               5                   10                  15

Gln Ala Asp Glu Met Gln Arg Tyr Val Glu Glu Asn Gln Thr Arg Asn
                20                  25                  30

Lys His Ile Asn Pro Asn Glu Trp Trp Lys Val Tyr Pro Ser Ser Val
            35                  40                  45

Thr Glu Phe Lys Phe Leu Phe Val Ser Gly His Phe Lys Gly Asn Tyr
        50                  55                  60

Lys Ala Gln Leu Thr Arg Leu Asn His Ile Thr Asn
65                  70                  75

<210> SEQ ID NO 24
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 24
ctacccataa taatggactg tccccttctg ggctcactat gctgccgccc agccatgatg    60
atggaagcag                                                          70

<210> SEQ ID NO 25
<211> LENGTH: 66
<212> TYPE: DNA
<213> ORGANISM: Homo sapiens

<400> SEQUENCE: 25
tttttccttc ttactgtccc cttctgggct cactatgctg ccgcccagtg ggactttgga    60
aataca                                                              66

<210> SEQ ID NO 26
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tttttccttc ttactgtccc cttctgggct cactatatgc tgccgcccag tgggactttg    60
gaaata                                                              66

<210> SEQ ID NO 27
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tttttccttc ttactgtccc cttctgggcg ctgccgccca gtgggacttt ggaaataca    59

<210> SEQ ID NO 28
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tttttccttc ttactgtccc cttctgggcg ggctcactat gctgccgccc agtgggactt    60
tggaaa                                                              66

<210> SEQ ID NO 29
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tttttccttc ttactgtccc cttctgggct cactatgctg ctgccgccca gtgggactttg   60 ggaaat                                                              66

<210> SEQ ID NO 30
<211> LENGTH: 62
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tttttccttc ttactgtccc cttcctcact atgctgccgc ccagtgggac tttggaaata      60
ca                                                                    62

<210> SEQ ID NO 31
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tttttccttc ttactgtccc cttcctatgc tgccgcccag tgggactttg gaaataca       58

<210> SEQ ID NO 32
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tttttccttc ttactgtccc cttcctgccg cccagtggga ctttggaaat aca            53

<210> SEQ ID NO 33
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tttttccttc ttactgtccc cttctgggct catcactatg ctgccgccca gtgggacttt     60
ggaaat                                                                66

<210> SEQ ID NO 34
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tttttccttc ttactgtccc cttctgggct cactattatg ctgccgccca gtgggacttt     60
ggaaat                                                                66

<210> SEQ ID NO 35
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

```
tttttccttc ttactgtccc cttctgggct cactattatg ctgccgccca gtgggacttt      60
ggaaat                                                                  66
```

<210> SEQ ID NO 36
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

```
tttttccttc ttactgtccc cttctgggct ctgccgccca gtgggacttt ggaaataca       59
```

<210> SEQ ID NO 37
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

```
tttttccttc ttactgtccc cttctgggct ctcactatgc tgccgcccag tgggactttg      60
gaaata                                                                  66
```

<210> SEQ ID NO 38
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

```
tttttccttc ttactgtccc cttctggtgc tgccgcccag tgggactttg gaaataca        58
```

<210> SEQ ID NO 39
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

```
tttttccttc ttactgtccc cttctgggct cacgctgccg cccagtggga ctttggaaat      60
aca                                                                     63
```

<210> SEQ ID NO 40
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

```
tttttccttc ttactgtccc cttctgggct cagccgccca gtgggacttt ggaaataca       59
```

<210> SEQ ID NO 41
<211> LENGTH: 52
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 41
tttttccttc ttactgtccc cttctgccgc ccagtgggac tttggaaata ca            52

<210> SEQ ID NO 42
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tttttccttc ttactgtccc cttctgggct cacttcacta tgctgccgcc cagtgggact    60
ttggaa                                                              66

<210> SEQ ID NO 43
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tttttccttc ttactgtccc cttctgggtg ccgcccagtg ggactttgga aataca        56

<210> SEQ ID NO 44
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cagccgctac ccataataat gggtcatcct catcctgata aactgcaaaa gccatgatga    60
tggaagcagc acga                                                     74

<210> SEQ ID NO 45
<211> LENGTH: 66
<212> TYPE: DNA
<213> ORGANISM: Homo sapiens

<400> SEQUENCE: 45
gggcaacatg ctggtcatcc tcatcctgat aaactgcaaa aggctgaaga gcatgactga    60
catcta                                                              66

<210> SEQ ID NO 46
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gggcaacatg ctggtcatcc tcatccaact gcaaaaggct gaagagcatg actgacatct    60
a                                                                   61

<210> SEQ ID NO 47

```
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gggcaacatg ctggtcatcc tcatcctgat aaaaactgca aaaggctgaa gagcatgact        60
gacatc                                                                   66

<210> SEQ ID NO 48
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gggcaacatg ctggtcatcc tcatactgca aaaggctgaa gagcatgact gacatcta          58

<210> SEQ ID NO 49
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gggcaacatg ctggtcatcc tcatcctaaa ctgcaaaagg ctgaagagca tgactgacat        60
cta                                                                      63

<210> SEQ ID NO 50
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gggcaacatg ctggtcatcc tcatcctgat gataaactgc aaaaggctga agagcatgac        60
tgacat                                                                   66

<210> SEQ ID NO 51
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gggcaacatg ctggtcatcc tcatcctgat tgcaaaaggc tgaagagcat gactgacatc        60
ta                                                                       62

<210> SEQ ID NO 52
<211> LENGTH: 10
<212> TYPE: DNA
<213> ORGANISM: Homo sapiens
```

```
<400> SEQUENCE: 52
gctgccgccc                                                                10

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gaacgcggaa cgctggcccg c                                                   21

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Arg Gly Thr Leu Ala Arg
1               5

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gaccgctcgg acttgacgcg c                                                   21

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Arg Ser Asp Leu Thr Arg
1               5

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
caatcctctg acttgacgcg c                                                   21

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 58

Gln Ser Ser Asp Leu Thr Arg
1               5

<210> SEQ ID NO 59
<211> LENGTH: 10
<212> TYPE: DNA
<213> ORGANISM: Homo sapiens

<400> SEQUENCE: 59 gaagggggaca                                                         10

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gacagatcca accttacccg c                                             21

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asp Arg Ser Asn Leu Thr Arg
1               5

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cgcagcgatc atctcaccaa a                                             21

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Ser Asp His Leu Thr Lys
1               5

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 64
caatcctcta atctcgctcg c                                          21

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Ser Ser Asn Leu Ala Arg
1               5

<210> SEQ ID NO 66
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Leu Asp Ser Lys Ala Tyr Ser Glu Gly Phe Pro Leu Thr Ala Ser His
1               5                   10                  15

Thr Arg Ala Met Glu Arg Tyr Leu Arg Gln Phe Thr Gly Arg Lys Glu
            20                  25                  30

Glu Leu Lys Pro Thr Trp Trp Asp Ile Ala Pro Glu His Leu Asp Asn
        35                  40                  45

Thr Tyr Phe Ala Tyr Val Ser Gly Ser Ser Phe Ser Gly Asn Tyr Lys
    50                  55                  60

Glu Gln Leu Gln Lys Phe Arg Gln Asp Thr
65                  70

<210> SEQ ID NO 67
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ile Leu Asp Ser Lys Ala Tyr Ser Glu Gly Phe Pro Leu Thr Ala Ser
1               5                   10                  15

His Thr Asp Ala Met Gly Asp Tyr Leu Lys Gln Phe Thr Glu Arg Lys
            20                  25                  30

Glu Glu Ile Lys Pro Thr Trp Trp Asp Ile Ala Pro Glu His Leu Asp
        35                  40                  45

Asn Thr Tyr Phe Ala Tyr Val Ser Gly Ser Phe Ser Gly Asn Tyr Lys
    50                  55                  60

Glu Gln Leu Gln Lys Phe Arg Gln Lys Thr
65                  70

<210> SEQ ID NO 68
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 68

Leu Asp Ser Lys Ala Tyr Ser Glu Gly Phe Pro Leu Thr Ala Ser His
1               5                   10                  15

Thr Arg Ala Met Glu Arg Tyr Leu Arg Gln Phe Thr Glu Arg Lys Glu
                20                  25                  30

Glu Leu Lys Pro Thr Trp Trp Asp Ile Ala Pro Glu His Leu Asp Asn
            35                  40                  45

Thr Tyr Phe Ala Tyr Val Ser Gly Ser Ser Phe Ser Gly Asn Tyr Lys
        50                  55                  60

Glu Gln Leu Gln Lys Phe Arg Gln Asp Thr
65                  70

<210> SEQ ID NO 69
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ile Leu Asp Ser Lys Ala Tyr Ser Glu Gly Phe Pro Leu Thr Ala Ser
1               5                   10                  15

His Thr Asp Ala Met Gly Asp Tyr Leu Lys Gln Phe Thr Glu Arg Lys
                20                  25                  30

Glu Glu Ile Lys Pro Thr Trp Trp Asp Ile Ala Pro Glu His Leu Asp
            35                  40                  45

Asn Thr Tyr Phe Ala Tyr Val Ser Gly Ser Ser Phe Ser Gly Asn Tyr Lys
        50                  55                  60

Glu Gln Leu Gln Lys Phe Arg Gln Lys Thr
65                  70
```

OBLIGATE HETERODIMER VARIANTS OF FOKI CLEAVAGE DOMAIN

The present application is a U.S. National Phase application of and claims priority from PCT/US2011/045558, filed on 27 Jul. 2011 designating the United States, which in turn was based on and claims priority from U.S. Provisional Patent Application Nos. 61/368,024 filed 27 Jul. 2010 all of which applications are incorporated herein by reference.

The research resulting in the invention described herein was supported in part by funding from the National Institutes of Health GM077291. The United States Government has certain rights in the invention.

BACKGROUND

There have emerged powerful tools, e.g., Zinc finger nucleases (ZFNs) and transcription activator-like effector nucleases (TALENs), for delivering a targeted genomic double-strand break (DSB) to either stimulate local homologous recombination (HR) with investigator-provided donor DNA or induce gene mutations at the site of cleavage in absence of a donor by non-homologous end joining (NHEJ), both in plant and mammalian cells, including human cells. ZFNs or TALENs are formed by fusing zinc finger proteins (ZFPs) or transcription activator-like effectors (TALEs) to the non-specific cleavage domain of FokI restriction enzyme. ZFN-mediated (or TALEN-mediated) gene targeting yields high gene modification efficiencies (>10%), in a variety of cells and cell types by delivering a recombinogenic DSB to the targeted chromosomal locus, using two designed ZFNs (or TALENs). Mechanism of DSB by ZFNs (or TALENs) requires that two ZFN (or TALEN) monomers bind to their adjacent cognate sites on DNA and the FokI nuclease domains dimerize to form the active catalytic center for the induction of the DSB. In the case of ZFNs (or TALENs) fused to wild-type FokI cleavage domains, homodimers may also form, which could limit the efficacy and safety of the ZFNs (or TALENs) by inducing off-target cleavage. Obligate heterodimer variants of FokI cleavage domain for creating custom ZFNs (or TALENs) are known.

However, there is a need for more efficacy and efficiency of the re-engineered obligate heterodimer variants of FokI cleavage domain with minimal cellular toxicity.

BRIEF DESCRIPTION OF THE DRAWINGS

FIG. 1 shows the amino acid and DNA sequence for FokI nuclease domain mutant REL.

FIG. 2 shows the amino acid and DNA sequence for FokI nuclease domain mutant DKK.

FIG. 3 shows the amino acid and DNA sequence for FokI nuclease domain mutant RVEL.

FIG. 4 shows the amino acid and DNA sequence for FokI nuclease domain mutant DKAK.

FIG. 5 shows the amino acid and DNA sequence for FokI nuclease domain variant with StsI segment containing REL mutations.

FIG. 6 shows the amino acid and DNA sequence for FokI nuclease domain variant with StsI segment containing DKK mutations.

FIG. 7 shows the amino acid and DNA sequence for FokI wild-type nuclease domain.

FIG. 8 shows the amino acid and DNA sequence for FokI nuclease domain mutant DA (Cathoman Lab).

FIG. 9 shows the amino acid and DNA sequence for FokI nuclease domain mutant RV (Cathoman Lab).

FIG. 10 shows the amino acid and DNA sequence for FokI nuclease domain mutant EL (Sangamo).

FIG. 11 shows the amino acid and DNA sequence for FokI nuclease domain mutant KK (Sangamo).

FIG. 12 shows the amino acid sequence containing the α4 and α5 helices that mediate dimerization between two monomers of the FokI cleavage domains with the corresponding segment from StsI, an isoschizomer of FokI endonuclease.

DESCRIPTION

Figure 13:
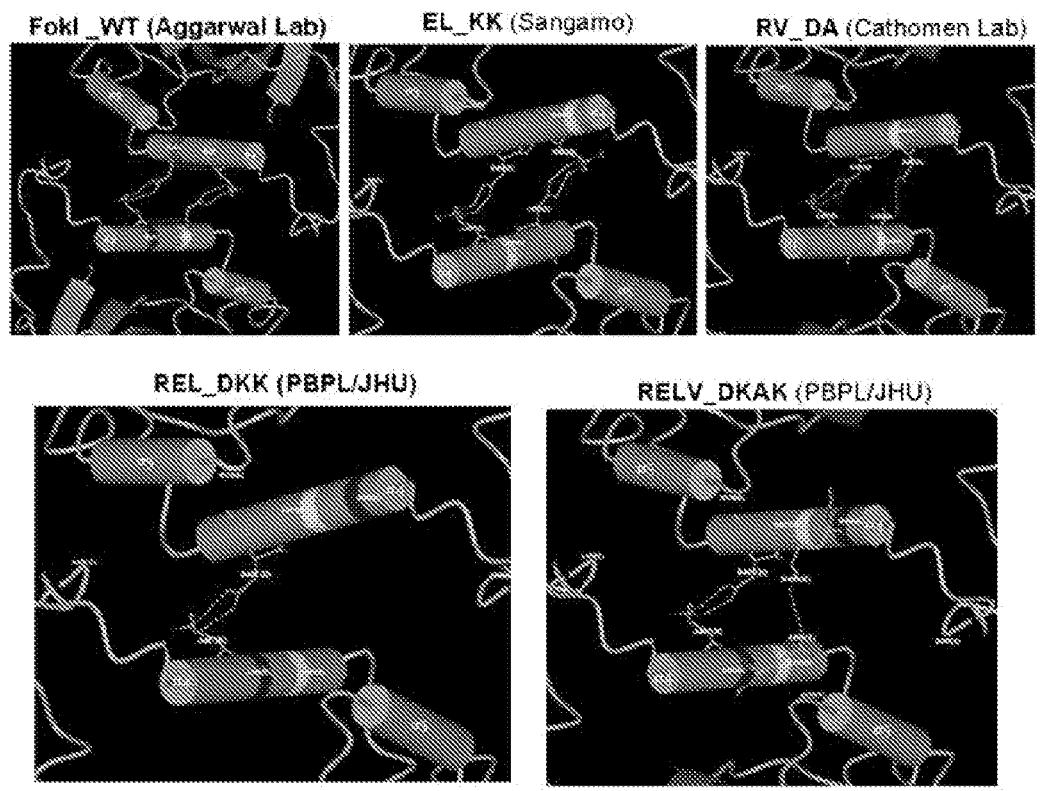
FIG. 13 shows predicted profiles of H-bond interactions between α4 helices at the dimer interface of obligate heterodimer variants of FokI nuclease domains, based on protein modeling and energy minimization. The 3D structure of the FokI dimer was obtained from RCSB Protein Data Bank, which was generated by X-ray diffraction method at a resolution of 2.3 A° by Aggarwaal's lab (36). The CCP4 Molecular Graphics software (Version 6.1.2) for Macromolecular X-ray Crystallography was used for 3D structure analysis and SPDBV software for protein modeling. Only hydrogen bond interactions between α4 helices at the dimer interface are shown. All potential dimer interface interactions (H-bond interactions and hydrophobic interactions) are listed in Table 2.

Disclosed herein are polypeptides comprising an engineered FokI cleavage domain variant comprising a mutation in at least three or more wild-type amino acid residues, the engineered FokI cleavage domain variant forming an obligate heterodimer with a second engineered FokI cleavage domain variant with at least one different mutation in one or more wild-type amino acid residues.

In particular embodiments, disclosed are fusion polypeptides containing the engineered FokI cleavage domain variants useful for targeted cleavage of cellular chromatin and for targeted alteration of a cellular nucleotide sequence, e.g., by targeted cleavage followed by non-homologous end joining or by targeted cleavage followed by homologous recombination between an exogenous polynucleotide (comprising one or more regions of homology with the cellular nucleotide sequence) and a genomic sequence.

Exemplary engineered FokI cleavage domain variant are shown in FIGS. 1-6. The variants in include at least three mutations such that they form heterodimers with each other, but not homodimers. This increases the specificity of DNA cleavage and/or increases the concentration of the intended complex (by reducing or eliminating competition from homodimers). When incorporated into fusion proteins, such as zinc finger nucleases (ZFN) and transcription activator-like effector nucleases (TALENs), these variants induce gene modification at the intended target (both at an endogenous locus and when tested using an integrated GFP reporter assay) while significantly reducing genome-wide off-target DNA cleavage as compared to wild-type FokI cleavage domain variant.

Thus, the engineered FokI cleavage domain variant described herein significantly impair homodimer function, since forcing two copies of the same variant to interact reduces or abolishes gene modification. Reduced homodimer function provides improved ZFN or TALEN cleavage specificity in vivo, without any decrease in either ZFN or TALEN expression or the ability to stimulate modification of the desired target site.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower K.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins or TALE have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data.

A "selected" zinc finger protein is a protein not found in nature whose production results primarily from an empirical process such as phage display, interaction trap or hybrid selection.

Examples of Designed Zinc Finger Nucleases can be found in US Published Patent Application No. 2010/0055793.

Transcription activator-like effector (TALE) protein (or binding domain) is a protein, or a domain within a larger protein, that binds DNA in a sequence-specific manner. Transcription activator-like effector (TALE) domains can be "engineered" to bind to a predetermined nucleotide sequence. Examples of TALE proteins and domains can be found in Miller et al., A TALE nuclease architecture for efficient genome editing, Nat. Biotechnol. 2011 February; 29(2):143-8. Epub 2010 Dec. 22; and Hockemeyer et al., Genetic engineering of human pluripotent cells using TALE nucleases, Nat. Biotechnol. 2011 Jul. 7. doi: 10.1038/nbt.1927.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value there between or there above), preferably between about 100 and 1,000 nucleotides in length (or any integer there between), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination there between, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; Nucleic Acid Hybridization: A Practical Approach, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule Inhibition of hybridization of the completely identical sequence can be assessed using hybridization assays that are well known in the art (e.g., Southern (DNA) blot, Northern (RNA) blot, solution hybridization, or the like, see Sambrook, et al., Molecular Cloning: A Laboratory Manual, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, Nucleic Acid Hybridization: A Practical Approach, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., Molecular Cloning: A Laboratory Manual, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. Proteins include, but are not limited to, DNA-binding proteins, transcription factors, chromatin remodeling factors, methylated DNA binding proteins, polymerases, methylates, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "FokI cleavage domain variant" is a polypeptide sequence which can, in conjunction with a second polypeptide (either identical or different) form a complex having cleavage activity (preferably double-strand cleavage activity). The terms "first and second FokI cleavage domain variant;" "+ and − FokI cleavage domain variant" and "right and left FokI cleavage domain variant" are used interchangeably to refer to pairs of FokI cleavage domain variant that dimerize. In particular embodiments, the FokI cleavage domain variant may be referred to as a half-domain FokI cleavage variant. FokI restriction endonucleases have been described in U.S. Pat. Nos. 5,356,802, 5,436,150, 5,487,994, 5,792,640, 5,916,794, and 6,265,196.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Eucaryotic" cells include, but are not limited to, fungal cells (such as yeast), plant cells, animal cells, mammalian cells and human cells.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP or TALE DNA-binding domain is fused to a cleavage domain, the ZFP or the TALE DNA-binding domain and the cleavage domain are in operative linkage if, in the fusion polypeptide, the ZFP or TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246.

An "engineered FokI cleavage domain variant" is a FokI cleavage domain that has been modified so as to form obligate heterodimers with another FokI cleavage domain variant (e.g., another engineered FokI cleavage domain variant). Engineered FokI cleavage domain variant (also be referred to as dimerization domain mutants) minimize or prevent homodimerization. Amino acid residues at positions 446, 447, 479, 483, 484, 486, 487, 490, 491, 496, 498, 499, 500, 531, 534, 537, and 538 of FokI all can be targets for influencing dimerization of the FokI cleavage domain variants. Numbering of amino acid residues in the FokI protein is according to Wah et al., (1998) Proc Natl Acad Sci USA 95:10564-10569.

Described herein are engineered FokI cleavage domain variants that contain a mutation in at least three or more wild-type amino acid residues and that form an obligate heterodimer. Exemplary mutant FokI cleavage domain variants are shown in FIGS. 1-6. In certain embodiments, the FokI cleavage domain variant includes mutations in at least three amino acid residues at positions 483, 486, 487, 490, 499 or 538 of wild-type FokI, see FIGS. 1-4 and Examples.

Specifically, the engineered FokI cleavage domain variants, described herein, were prepared by mutating certain positions in a wild-type FokI cleavage domain sequence to produce an engineered FokI cleavage domain variant.

Examples of the engineered FokI cleavage domain variant, may include the polypeptide designated D483R:Q486E:I499L (SEQ ID NO: 1), the polypeptide designated R487D:E490K:I538K (SEQ ID NO: 3), the polypeptide designated D483R:Q486E:I499L:I538V (SEQ ID NO: 5), or the polypeptide designated R487D:E490K:I499A:I538K (SEQ ID NO: 7).

In further embodiments, the engineered FokI cleavage domain variant may include the polypeptide designated:

```
                                           (SEQ ID NO: 66)
LDSKAYSEGFPLTASHTRAMERYLRQFTERKEELKPTWWDIAPEHLDN

TYFAYVSGSSFSGNYKEQLQKFRQDT,
or the polypeptide designated:

(SEQ ID NO: 67)
ILDSKAYSEGFPLTASHTDAMGDYIKQFTERKEEIKPTWWDIAPEHLD

NTYFAYVSGSFSGNYKEQLQKFRQKT.
```

In certain aspects, the segment from the wild-type FokI cleavage domain variant,

```
                                           (SEQ ID NO: 23)
IVDTKAYSGGYNLPIGQADEMQRYVEENQTRNKHINPNEWWKVYPSSVT

EFKFLFVSGHFKGNYKAQLTRLNHITN,
is replaced with the polypeptide designated:

(SEQ ID NO: 66)
LDSKAYSEGFPLTASHTRAMERYLRQFTERKEELKPTWWDIAPEHLDN

TYFAYVSGSSFSGNYKEQLQKFRQDT,
or the polypeptide designated:

(SEQ ID NO: 67)
ILDSKAYSEGFPLTASHTDAMGDYIKQFTERKEEIKPTWWDIAPEHLD

NTYFAYVSGSFSGNYKEQLQKFRQKT.
```

Engineered FokI cleavage domain variants described herein can be prepared using any suitable method, for example, by site-directed mutagenesis of wild-type FokI cleavage domain variant (FokI) as described in the examples. The engineered FokI cleavage domain variants described herein are obligate heterodimer mutants in which aberrant cleavage is minimized or abolished.

In yet other embodiments, disclosed are heterodimers made up of a first engineered FokI cleavage domain variant including a mutation in at least three or more wild-type amino acid residues, and a second different engineered FokI cleavage domain variant with at least one different mutation in one or more wild-type amino acid residues. In certain embodiments, the mutations may be in at least three amino acid residues at positions 483, 486, 487, 490, 499 or 538 of wild-type FokI. In certain aspects the heterodimers are made up of a first engineered FokI cleavage domain variant including a mutation in at least three or more wild-type amino acid residues, and a second different engineered FokI cleavage domain variant with different mutations in three or more wild-type amino acid residues.

In certain embodiments, the heterodimer may include a first engineered FokI cleavage domain variant that is different from the second engineered FokI cleavage domain variant, and both independently contain a polypeptide selected from the polypeptide designated D483R:Q486E:I499L (SEQ ID NO: 1), the polypeptide designated R487D:E490K:I538K (SEQ ID NO: 3), the polypeptide designated D483R:Q486E:I499L:I538V (SEQ ID NO: 5) or the polypeptide designated R487D:E490K:I499A:I538K (SEQ ID NO: 7).

In an exemplary embodiment, the heterodimer is made up of an engineered FokI cleavage domain variant containing the polypeptide designated D483R:Q486E:I499L (SEQ ID NO: 1), and the other containing the polypeptide designated R487D:E490K:I538K (SEQ ID NO: 3).

In certain aspects, the obligate heterodimer may include a first monomer containing the polypeptide designated D483R:Q486E:I499L (SEQ ID NO: 1), and a second monomer containing the polypeptide designated R487D:E490K:I538K (SEQ ID NO: 3). In yet other aspects, the obligate heterodimer may include a first monomer containing the polypeptide designated D483R:Q486E:I499L:I538V (SEQ ID NO: 5), and a second monomer containing the polypeptide designated R487D:E490K:I499A:I538K (SEQ ID NO: 7).

In yet other aspects, the obligate heterodimer may include a first monomer containing the polypeptide designated:

```
                                           (SEQ ID NO: 66)
LDSKAYSEGFPLTASHTRAMERYLRQFTERKEELKPTWWDIAPEHLDN

TYFAYVSGSSFSGNYKEQLQKFRQDT,
and a second monomer containing the polypeptide
designated:

(SEQ ID NO: 67)
LDSKAYSEGFPLTASHTDAMGDYIKQFTERKEEIKPTWWDIAPEHLDN

TYFAYVSGSFSGNYKEQLQKFRQKT.
```

In other embodiments, the engineered FokI cleavage domain variant described herein are advantageously used in fusion proteins with a DNA-binding domain, such as zinc finger proteins (ZFPs) or transcription activator-like effector (TALE) proteins, to specifically target sites for cleavage in any cell.

In certain embodiments, the fusion protein may include a DNA-binding domain and at least one engineered FokI cleavage domain variant comprising a mutation in at least three or more wild-type amino acid residues, the engineered FokI cleavage domain variant forming an obligate heterodimer with a second engineered FokI cleavage domain variant with at least one different mutation in one or more wild-type amino acid residues. The DNA-binding domain may include zinc finger protein (ZFP) or transcription activator-like effector (TALE) protein domains.

In further embodiments, disclosed are methods for making and using the engineered FokI cleavage domain variants, the obligate heterodimer containing two FokI cleavage domain variants, and the fusion protein containing the obligate heterodimer containing two FokI cleavage domain variants and DNA binding domains containing, e.g., ZFPs or TALEs, as described below.

ZFNs or TALENs and methods for design and construction of fusion proteins (and polynucleotides encoding same) are known to those of skill in the art. The ZFNs or TALEs described herein may be delivered to a target cell by any suitable means. Methods of delivering proteins comprising ZFNs or TALENs are described. ZFNs or TALENs as described herein may also be delivered using vectors containing sequences encoding one or more ZFNs or TALENs. Any vector systems may be used including, but not limited to, plasmid vectors, retroviral vectors, lentiviral vectors, adenovirus vectors, poxvirus vectors; herpesvirus vectors and adeno-associated virus vectors, etc.

Conventional viral and non-viral based gene transfer methods can be used to introduce nucleic acids encoding ZFNs or TALENs comprising engineered cleavage domains in cells (e.g., mammalian cells) and target tissues. Such methods can also be used to administer such nucleic acids to cells in vitro. In certain embodiments, nucleic acids encoding ZFNs or TALENs are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, Science 256:808-813 (1992); Nabel & Feigner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds.) (1995); and Yu et al., Gene Therapy 1:13-26 (1994).

Methods of non-viral delivery of nucleic acids encoding ZFNs or TALENs include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (RichMar) can also be used for delivery of nucleic acids. Additional exemplary nucleic acid delivery systems include those provided by Amaxa Biosystems (Cologne, Germany), Maxcyte, Inc. (Rockville, Md.) and BTX Molecular Delivery Systems (Holliston, Mass.). Lipofection and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); and Ahmad et al., Cancer Res. 52:4817-4820 (1992).

The use of RNA or DNA viral based systems for the delivery of nucleic acids encoding ZFNs or TALENs comprising engineered FokI cleavage domain variant as described herein take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFNs or TALENs include, but are not limited to, retroviral, lentiviral, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., J. Virol. 66:2731-2739 (1992); Johann et al., J. Virol. 66:1635-1640 (1992); Sommerfelt et al., Virol. 176:58-59 (1990); Wilson et al., J. Virol. 63:2374-2378 (1989); Miller et al., J. Virol. 65:2220-2224 (1991); PCT/U594/05700).

In applications in which transient expression of a pair of ZFN or TALEN fusion proteins is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., Blood 85:3048-305 (1995); Kohn et al., Nat. Med. 1:1017-102 (1995); Malech et al., PNAS 94:22 12133-12138 (1997)). PA317/pLASN was the first therapeutic vector used in a gene therapy trial. (Blaese et al., Science 270:475-480 (1995)). Transduction efficiencies of 50% or greater have been observed for MFG-S packaged vectors. (Ellem et al., Immunol Immunother. 44(1):10-20 (1997); Dranoff et al., Hum. Gene Ther. 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3 (1998), Kearns et al., Gene Ther. 9:748-55 (1996)).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., Hum. Gene Ther. 7:1083-9 (1998)). Additional examples of the use of adenovirus vectors for gene transfer in clinical trials include Rosenecker et al., Infection 24:1 5-10 (1996); Sterman et al., Hum. Gene Ther. 9:7 1083-1089 (1998); Welsh et al., Hum. Gene Ther. 2:205-18 (1995); Alvarez et al., Hum. Gene Ther. 5:597-613 (1997); Topf et al., Gene Ther. 5:507-513 (1998); Sterman et al., Hum. Gene Ther. 7:1083-1089 (1998).

In certain embodiments, the vector is an adenovirus vector. Thus, described herein are adenovirus (Ad) vectors for introducing heterologous sequences (e.g., ZFNs or TALENs) into cells.

Non-limiting examples of Ad vectors that can be used in the present application include recombinant (such as E1-deleted), conditionally replication competent (such as oncolytic) and/or replication competent Ad vectors derived from human or non-human serotypes (e.g., Ad5, Ad11, Ad35, or porcine adenovirus-3); and/or chimeric Ad vectors (such as Ad5/35) or tropism-altered Ad vectors with engineered fiber (e.g., knob or shaft) proteins (such as peptide insertions within the HI loop of the knob protein). Also useful are "gutless" Ad vectors, e.g., an Ad vector in which all adenovirus genes have been removed, to reduce immunogenicity and to increase the size of the DNA payload. This allows, for example, simultaneous delivery of sequences encoding ZFNs or TALENs and a donor sequence. Such gutless vectors are especially useful when the donor sequences include large transgenes to be integrated via targeted integration.

Replication-deficient recombinant adenoviral vectors (Ad) can be produced at high titer, and they readily infect a number of different cell types. Most adenovirus vectors are engineered such that a transgene replaces the Ad E1a, E1b, and/or E3 genes; subsequently the replication defective vector is propagated in cells that provide one or more of the deleted gene functions in trans. For example, human 293 cells supply E1 function. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., Hum. Gene Ther. 7:1083-1089 (1998)).

Additional examples of the use of adenovirus vectors for gene transfer in clinical trials include Rosenecker et al., Infection 24:1 5-10 (1996); Welsh et al., Hum. Gene Ther. 2:205-18 (1995); Alvarez et al., Hum. Gene Ther. 5:597-613 (1997); Topf et al., Gene Ther. 5:507-513 (1998).

In certain embodiments, the Ad vector is a chimeric adenovirus vector, containing sequences from two or more different adenovirus genomes. For example, the Ad vector can be an Ad5/35 vector. Ad5/35 is created by replacing one or more of the fiber protein genes (knob, shaft, tail, penton) of Ad5 with the corresponding fiber protein gene from a B group adenovirus such as, for example, Ad35. The Ad5/35 vector and characteristics of this vector are described, for example, in Ni et al. (2005) "Evaluation of biodistribution and safety of adenovirus vectors containing group B fibers after intravenous injection into baboons," Hum Gene Ther 16:664-677; Nilsson et al. (2004) "Functionally distinct subpopulations of cord blood CD34+ cells are transduced by adenoviral vectors with serotype 5 or 35 tropism," Mol Ther 9:377-388; Nilsson et al. (2004) "Development of an adenoviral vector system with adenovirus serotype 35 tropism; efficient transient gene transfer into primary malignant hematopoietic cells," J Gene Med 6:631-641; Schroers et al. (2004) "Gene transfer into human T lymphocytes and natural killer cells by Ad5/F35 chimeric adenoviral vectors," Exp Hematol 32:536-546; Seshidhar et al. (2003) "Development of adenovirus serotype 35 as a gene transfer vector," Virology 311:384-393; Shayakhmetov et al. (2000) "Efficient gene transfer into human CD34(+) cells by a retargeted adenovirus vector," J Virol 74:2567-2583; and Soya et al. (2004), "A tumor-targeted and conditionally replicating oncolytic adenovirus vector expressing TRAIL for treatment of liver metastases," Mol Ther 9:496-509.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., Proc. Natl. Acad. Sci. USA 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFNs or TALENs nucleic acid (gene or cDNA), and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., J. Exp. Med. 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., J. Exp. Med. 176:1693-1702 (1992)).

Vectors (e.g., retroviruses, adenoviruses, liposomes, etc.) containing therapeutic ZFNs or TALENs nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are known and Vectors useful for introduction of transgenes into hematopoietic stem cells, e.g., CD34+ cells, include adenovirus Type 35. Vectors suitable for introduction of transgenes into immune cells (e.g., T-cells) include non-integrating lentivirus vectors. See, for example, Ory et al. (1996) Proc. Natl. Acad. Sci. USA 93:11382-11388; Dull et al. (1998) J. Virol. 72:8463-8471; Zuffery et al. (1998) J. Virol. 72:9873-9880; Follenzi et al. (2000) Nature Genetics 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, W138, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pischia* and *Schizosaccharomyces*. Progeny, variants and derivatives of these cell lines can also be used.

The disclosed cleavage domains are advantageously used in combination with zinc finger proteins or transcription activator-like effector (TALE) proteins to cleave DNA and minimize off-target site cleavage (as compared to ZFNs or TALENs comprising wild-type or homodimerizing cleavage domains). Cleavage can be at a region of interest in cellular chromatin (e.g., at a desired or predetermined site in a genome, for example, in a gene, either mutant or wild-type); to replace a genomic sequence (e.g., a region of interest in cellular chromatin) with a homologous non-identical sequence (i.e., targeted recombination); to delete a genomic sequence by cleaving DNA at one or more sites in the genome, which cleavage sites are then joined by non-homologous end joining (NHEJ); to screen for cellular factors that facilitate homologous recombination; and/or to replace a wild-type sequence with a mutant sequence, or to convert one allele to a different allele.

Accordingly, the disclosed engineered FokI cleavage domain variant can be used in any ZFNs or TALENs for any method in which specifically targeted cleavage is desirable and/or to replace any genomic sequence with a homologous, non-identical sequence. For example, a mutant genomic sequence can be replaced by its wild-type counterpart, thereby providing methods for treatment of e.g., genetic disease, inherited disorders, cancer, and autoimmune disease. In like fashion, one allele of a gene can be replaced by a different allele using the methods of targeted recombination disclosed herein. Indeed, any pathology dependent upon a particular genomic sequence, in any fashion, can be corrected or alleviated using the methods and compositions disclosed herein.

Exemplary genetic diseases include, but are not limited to, achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6.sup.th codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted DNA cleavage and/or homologous recombination include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Such methods also allow for treatment of infections (viral or bacterial) in a host (e.g., by blocking expression of viral or bacterial receptors, thereby preventing infection and/or spread in a host organism); to treat genetic diseases.

Targeted cleavage of infecting or integrated viral genomes can be used to treat viral infections in a host. Additionally, targeted cleavage of genes encoding receptors for viruses can be used to block expression of such receptors, thereby preventing viral infection and/or viral spread in a host organism. Targeted mutagenesis of genes encoding viral receptors (e.g., the CCR5 and CXCR4 receptors for HIV) can be used to render the receptors unable to bind to virus, thereby preventing new infection and blocking the spread of existing infections.

Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors may be targeted, including, but not limited to, Picornaviridae (e.g., polioviruses, etc.); Caliciviridae; Togaviridae (e.g., rubella virus, dengue virus, etc.); Flaviviridae; Coronaviridae; Reoviridae; Bimaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses. Receptors for HIV, for example, include CCR5 and CXCR-4.

Among the genes which can be cleaved is CCR5 co-receptor (hCCR5) through which HIV gains entry into cells early in the infection. Thus, in one aspect, described herein are compositions and methods useful for disrupting the CCR5 gene in cells comprising an engineered fusion protein including zinc finger binding domain or transcription activator-like effector (TALE) domain to bind to a CCR5 target sequence and an engineered FokI cleavage domain variant, wherein said fusion protein binds to the CCR5 gene and cleaves the CCR5 gene. The mutation can be associated with any function of CCR5, e.g. the ability of an HIV virus to enter a host cell via the CCR5 co-receptor. CCR5 genes can be disrupted for a variety of purposes. For example, after cleavage of CCR5, the gene can be repaired by non-homologous end joining in the cell to give rise to a CCR5 gene mutation that inactivates the CCR5 receptor to produce HIV resistant cells. Alternatively, CCR5 receptor can be disrupted by replacing a wild type sequence with a CCR5Δ32 mutation. In one embodiment, a CCR5 chromosomal gene locus can serve as a "safe harbor" for the introduction of transgenes. That is, functions of CCR5 may be expendable, so that the gene can be cleaved and one of more therapeutic transgenes of interest can be inserted at the cleavage site for functional complementation in cells. In one embodiment, the CCR5 gene is a human gene, where one or more genes of interest can be introduced and expressed ectopically. These genes can be marker genes (e.g. neomycin or green fluorescent protein (GFP)) or genes applicable for human therapeutics.

In an exemplary embodiment, the fusion protein includes 3- or 4-zinc finger proteins (ZFP's) that target CCR5 of human cells, and the obligate heterodimer comprises a first monomer containing the polypeptide designated D483R: Q486E:I499L, and a second monomer containing the polypeptide designated R487D:E490K:I538K.

In particular embodiments, the zinc finger proteins (ZFPs) may include ZF1, ZF2, ZF3, ZF4, ZF5 or ZF6, described in Table 1.

TABLE 1

| ZF designs for the chosen targets within various mammalian genes | | | |
|---|---|---|---|
| Gene 5'-3' | ZFN target site | Triplet subsites 5'-3' | DNA coding sequence/contact residues -1 to +6 positions) of the α-helix for the ZF designs |
| hCCR5 | GCT GCC GCC c (SEQ ID NO: 52) | ZF1 GCC c | GAA CGC GGA ACG CTG GCC CGC (SEQ ID NO: 53) |
| | | | E R G T L A R (SEQ ID NO: 54) |
| | | ZF2 GCC g | GAC CGC TCG GAC TTG ACG CGC (SEQ ID NO: 55) |
| | | | D R S D L T R (SEQ ID NO: 56) |
| | | ZF3 GCT g | CAA TCC TCT GAC TTG ACG CGC (SEQ ID NO: 57) |
| | | | Q S S D L T R (SEQ ID NO: 58) |
| | GAA GGG GAC a (SEQ ID NO: 59) | ZF4 GAC a | GAC AGA TCC AAC CTT ACC CGC (SEQ ID NO: 60) |
| | | | D R S NL T R (SEQ ID NO: 61) |

TABLE 1-continued

ZF designs for the chosen targets within various mammalian genes

| Gene 5'-3' | ZFN target site | Triplet subsites 5'-3' | DNA coding sequence/contact residues -1 to +6 positions) of the α-helix for the ZF designs |
|---|---|---|---|
| | ZF5 | GGG g | CGC AGC GAT CAT CTC ACC AAA (SEQ ID NO: 62) |
| | | | R S D H L T K (SEQ ID NO: 63) |
| | ZF6 | GAA g | CAA TCC TCT AAT CTC GCT CGC (SEQ ID NO: 64) |
| | | | Q S S N L A R (SEQ ID NO: 65) |

In other embodiments, disclosed is a method of cleaving a gene of interest in a cell, the method comprising: providing a fusion protein comprising a DNA binding domain, e.g., zinc finger (ZF) binding domain or transcription activator-like effector (TALE) domain and an engineered FokI cleavage domain variant, wherein the zinc finger binding domain or transcription activator-like effector (TALE) domain binds to a target site in the gene of interest; and contacting the cell with the fusion protein under conditions such that the gene of interest is cleaved. In yet another embodiment, a composition is disclosed useful for disrupting a CCR5 gene in a cell, comprising an engineered fusion protein which comprises zinc finger (ZF) binding domain or transcription activator-like effector (TALE) domain to bind a gene of interest and an engineered FokI cleavage domain variant, wherein the fusion protein binds to and cleaves the gene of interest.

In particular embodiments, the gene of interest is CCR5, the zinc finger binding domain binds to a target site in the CCR5 gene, and the CCR5 gene is cleaved. In yet other aspects, the zinc finger binding domain comprises, as a recognition region, one of the six sequences shown for hCCR5 in Table 1. In yet another aspect, the recognition region of each of the three zinc fingers is ZF1, ZF2 or ZF3, or ZF4, ZF5 or ZF6.

Heterodimeric cleavage domain variants as described herein provide broad utility for improving ZFN or TALEN specificity in gene modification applications. These variant cleavage domains may be readily incorporated into any existing ZFN or TALEN by either site directed mutagenesis or subcloning to improve the in vivo specificity of any ZFN or TALEN dimers.

As noted above, the compositions and methods described herein can be used for gene modification, gene correction, and gene disruption. Non-limiting examples of gene modification includes homology directed repair (HDR)-based targeted integration; HDR-based gene correction; HDR-based gene modification; HDR-based gene disruption; NHEJ-based gene disruption and/or combinations of HDR, NHEJ, and/or single strand annealing (SSA). Single-Strand Annealing (SSA) refers to the repair of a double strand break between two repeated sequences that occur in the same orientation by resection of the DSB by 5'-3' exonucleases to expose the 2 complementary regions. The single-strands encoding the 2 direct repeats then anneal to each other, and the annealed intermediate can be processed such that the single-stranded tails (the portion of the single-stranded DNA that is not annealed to any sequence) are be digested away, the gaps filled in by DNA Polymerase, and the DNA ends rejoined. This results in the deletion of sequences located between the direct repeats.

Compositions comprising cleavage domains (e.g., ZFNs or TALENs) and methods described herein can also be used in the treatment of various genetic diseases and/or infectious diseases.

The compositions and methods can also be applied to stem cell based therapies, including but not limited to: (a) Correction of somatic cell mutations by short patch gene conversion or targeted integration for monogenic gene therapy; (b) Disruption of dominant negative alleles; (c) Disruption of genes required for the entry or productive infection of pathogens into cells; (d) Enhanced tissue engineering, for example, by: (i) Modifying gene activity to promote the differentiation or formation of functional tissues, and/or (ii) Disrupting gene activity to promote the differentiation or formation of functional tissues; (e) Blocking or inducing differentiation, for example, by: (i) Disrupting genes that block differentiation to promote stem cells to differentiate down a specific lineage pathway, (ii) Targeted insertion of a gene or siRNA expression cassette that can stimulate stem cell differentiation, (iii) Targeted insertion of a gene or siRNA expression cassette that can block stem cell differentiation and allow better expansion and maintenance of pluripotency, and/or (iv) Targeted insertion of a reporter gene in frame with an endogenous gene that is a marker of pluripotency or differentiation state that would allow an easy marker to score differentiation state of stem cells and how changes in media, cytokines, growth conditions, expression of genes, expression of siRNA molecules, exposure to antibodies to cell surface markers, or drugs alter this state; (f) Somatic cell nuclear transfer, for example, a patient's own somatic cells can be isolated, the intended target gene modified in the appropriate manner, cell clones generated (and quality controlled to ensure genome safety), and the nuclei from these cells isolated and transferred into unfertilized eggs to generate patient-specific hES cells that could be directly injected or differentiated before engrafting into the patient, thereby reducing or eliminating tissue rejection; and/or (g) Universal stem cells by knocking out MHC receptors—this approach would be used to generate cells of diminished or altogether abolished immunological identity. Cell types for this procedure include but are not limited to, T-cells, B cells, hematopoietic stem cells, and embryonic stem cells. Therefore, these stem cells or their derivatives (differentiated cell types or tissues) could be potentially engrafted into any person regardless of their origin or histocompatibility. (h) Targeted insertion of stem cell factor genes at a safe-harbor locus (CCR5 locus or AAVS1 site located on human chromosome PPP1R12c gene) within the human genome to reprogram cells to form induced pluripotent stem cells. (i) Targeted addition of therapeutic genes at a safe-harbor locus (CCR5 locus or AAVS1 site located on human chromosome PPP1R12c gene) within the human genome to provide functional protein complementation in cells with corresponding defective genes. (j) Targeted disruption of CCR5 by HDR or NHEJ to produce HIV resistant cells. (k) Genetic engineering of human pluripotent stem cells.

The compositions and methods can also be used for somatic cell therapy (e.g., autologus cell therapy and/or universal T-cell by knocking out MHC receptors, see section (g) above), thereby allowing production of stocks of T-cells that have been modified to enhance their biological properties. Such cells can be infused into a variety of patients independent of the donor source of the T-cells and their histocompatibility to the recipient.

In addition to therapeutic applications, the increased specificity provided by the variants described herein when used in ZFNs or TALENs can be used for crop engineering, cell line engineering and the construction of disease models. The obligate heterodimer FokI cleavage domain variant provide a straightforward means for improving ZFN and TALEN properties, especially when homodimer activity limits efficacy.

The engineered FokI cleavage domain variant described can also be used in gene modification protocols requiring simultaneous cleavage at multiple targets either to delete the intervening region or to alter two specific loci at once. Cleavage at two targets would require cellular expression of four ZFNs or TALENs, which would yield ten different active ZFN or TALEN combinations. For such applications, substitution of our variants for the wild-type nuclease domain would eliminate the activity of six of these combinations and reduce chances of off-target cleavage.

In particular embodiments, a method is disclosed for cleaving genomic cellular chromatin in a region of interest, the method comprising: (a) selecting a first nucleotide sequence in the region of interest; (b) engineering a first zinc finger binding domain or transcription activator-like effector (TALE) domain to bind to the first sequence; (c) expressing a first fusion protein in a cell, the first fusion protein comprising the engineered zinc finger binding domain or transcription activator-like effector (TALE) domain and an engineered FokI cleavage domain variant; (d) expressing a second fusion protein in the cell, the second fusion protein comprising a second zinc finger binding domain or transcription activator-like effector (TALE) domain and a second FokI cleavage domain variant; wherein the first fusion protein binds to the first nucleotide sequence, the second fusion protein binds to a second nucleotide sequence from the first nucleotide sequence on the complementary strand of DNA, the first and second engineered cleavage domains form a heterodimer that cleaves the cellular chromatin in the region of interest.

In another embodiment, a method is disclosed for reducing the formation of FokI cleavage domain variant homodimers, comprising engineering and using at least one FokI cleavage domain variant comprising a mutation in at least three or more wild-type amino acid residues to promote heterodimer formation. The method may include minimizing cytotoxicity and/or eliminating or greatly reducing cellular toxicity, by reducing off-target cleavage.

In yet another embodiment, a method for delivering a targeted genomic double-strand break (DSB) in cells is used, including plant, animal and human cells. The method may include: (a) selecting a first nucleotide sequence in the region of interest; (b) engineering a first zinc finger binding domain or transcription activator-like effector (TALE) domain to bind to the first sequence; (c) expressing a first fusion protein in a cell, the first fusion protein comprising the engineered zinc finger binding domain or transcription activator-like effector (TALE) domain and an engineered FokI cleavage domain variant; (d) expressing a second fusion protein in the cell, the second fusion protein comprising a second zinc finger binding domain or transcription activator-like effector (TALE) domain and a second FokI cleavage domain variant; wherein the first fusion protein binds to the first nucleotide sequence, the second fusion protein binds to a second nucleotide sequence from the first nucleotide sequence on the complementary strand of DNA, the first and second engineered cleavage domains form a heterodimer that cleaves the cellular chromatin in the region of interest.

In certain aspects, human cells may include sensitive human primary cells, human embryonic stem cells (hESC), adult human stem cells, human stem progenitor cells (hSPC) and human induced pluripotent stem cells (hiPSC). In yet other embodiments, method may further include delivering either stimulate local homologous recombination (HR) with investigator-provided donor DNA or inducing gene mutations at the site of cleavage in the absence of a donor by non-homologous end joining (NHEJ) in cells.

In certain embodiments, a polynucleotide is disclosed encoding the polypeptide of engineered FokI cleavage domain variant, e.g., FIGS. 1-6. In yet other aspects, an isolated cell or cell line are disclosed comprising the polypeptide or the polynucleotide of the engineered FokI cleavage domain variant.

The invention is to be understood as not being limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All publications mentioned herein, including patents, published patent applications, and journal articles are incorporated herein by reference in their entireties including the references cited therein, which are also incorporated herein by reference.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

This application claims priority to U.S. provisional application No. 61/368,024, filed Jul. 27, 2010, which is hereby incorporated herein by reference in their entirety.

EXAMPLES

Introduction

The creation of custom-designed zinc finger nucleases (ZFNs), and hence the development of ZFN-mediated gene targeting, provides molecular biologists with the ability to site-specifically and permanently modify plant and mammalian genomes, including the human genome via homology-directed repair of a targeted genomic DSB (1-5). The ZFNs are inactive as monomers. Mechanism of DSB by ZFNs requires that two different ZFN monomers bind to their adjacent cognate sites on DNA and that the FokI nuclease domains dimerize to form the active catalytic center for the induction of the DSB (6,7). Since dimerization of the FokI cleavage domain is required to produce a DSB, binding of two 3- or 4-finger ZFN monomers (each recognizing a 9- or 12 bp inverted site) to adjacent sites is necessary for delivering a genomic DSB in cells. Such a pair of ZFNs effectively has an 18- or 24-bp recognition site, which is long enough to specify a unique genomic location in plant and mammalian cells, including human cells (8,9). Because the recognition specificities of the ZFPs can be easily manipulated experimentally, designer ZFNs offer a general way for targeted manipulation of the genomes of a variety of cells and cell types (5, 14-31).

ZFN-mediated gene modification has been successfully demonstrated in a variety of cells from diverse species like frog oocytes (5), *Drosophila* (14-16), nematodes (17), zebra fish (18-20), mice (21), rats (22,23), plants (24,25) and humans (21, 26-31). High rate of endogenous gene modification efficiencies (>10%) have been achieved using this approach (27). However, in the case of ZFNs fused to wild-type FokI cleavage domains (FokI_WT), homodimers may also form, which could limit the efficacy and safety of the ZFNs by inducing off-target cleavage (32-34). ZFNs toxicity resulting from off-target cleavage, particularly when using 3-finger ZFNs, has been reported to decrease the viability of targeted cells. Two different approaches have been developed to reduce the cytotoxicity of ZFNs to cells: 1) Structure-based redesign of FokI cleavage domains at dimer interface to create obligate heterodimer variants that retained the wild type (WT) catalytic activity of natural FokI enzyme, but show reduced off-target cleavage, which is discussed below (32-34); and 2) Attenuation of ZFN toxicity by small-molecule regulation of protein levels in cells (35). The latter strategy, involves creating ZFNs with shortened half-lives by destabilizing ZFNs either by linking to a ubiquitin moiety to the N-terminus and then regulating ZFN levels by using a small molecule proteosome inhibitor or linking a modified destabilizing FKBP12 domain to the N-terminus and then regulating ZFN levels by using a small molecule that blocks destabilization effect of the N-terminal domain. Thus, it appears that by regulating ZFN levels one could maintain high rates of ZFN-mediated gene targeting while reducing ZFN toxicity.

Here, we report further improvements to obligate heterodimer variants of FokI cleavage domain for creating designer ZFNs with minimal cellular toxicity.

Example 1

Materials and Methods

Construction of ZFNs and the Donor Plasmid Substrate

The design and synthesis of CCR5-specific 3- and 4-finger ZFNs are described in references 21 and 28. The obligate heterodimer variants of FokI cleavage domain were constructed using overlapping oligonucleotides as described in reference 21. The nucleotide and protein sequences of the various obligate heterodimer variant pairs of FokI cleavage domain are shown in Table 2. Construction of the mutant eGFP genes encoding the desired ZFN target sites and the donor substrate for eGFP gene correction are described in references 21 and 27. The protocol for generating HEK293 cell lines with an integrated mutant eGFP gene encoding the desired ZFN target sites are described in references 21 and 27.

TABLE 2

Dimer Interface Interactions in Obligate Heterodimers of FokI Nuclease Domain Variants

| Redesign of FokI Dimer Interface Residues | Amino Acid Changes or Replacements | | H-bond Interactions | | H-bond Interactions | | H-bond Interactions | | Hydrophobic Interactions | |
|---|---|---|---|---|---|---|---|---|---|---|
| | Chain (A) | Chain (B) | (A) | (B) | (A) | (B) | (A) | (B) | (A) | (B) |
| FokI_WT (Aggarwal Lab)[1] | 483-Asp (D) 486-Gln (Q) 499-Ile (I) 538-Ile (I) | 487-Arg (R) 490-Glu (E) 499-Ile (I) 538-Ile (I) | R487-D483 (Bi-dentate) (2.7/2.7 A°) | | D483-R487 (Bi-dentate) (2.9/3.1 A°) | | Q486-E490 (Single H-bond) | | I499-I538 | |
| EL_KK (Sangamo)[2] | 486-Glu (E) 499-Leu (L) | 490-Lys (K) 538-Lys (K) | R487-D483 (Bi-dentate) (1.8/2.0 A°) | | D483-R487 (Bi-dentate) (2.3/2.0 A°) | | — | | — | |
| RV_DA (Cathomen Lab)[3] | 483-Arg (R) 499-Val (V) | 487-Asp (D) 538-Ala (A) | R487-D483 (Bi-dentate) (2.7/2.7 A°) | | R483-G480 (Single H-bond) (3.5 A°) | | Q486-D487 (Single H-bond) (3.8 A°) | | — | |
| REL_DKK (PBPL/JHU)[4] | 483-Arg (R) 486-Glu (E) 499-Leu (L) | 487-Asp (D) 490-Lys (K) 538-Lys (K) | R487-D483 (Bi-dentate) (2.7/2.7 A°) | | R483-G480 (Single H-bond) (2.2 A°) | | — | | — | |

TABLE 2-continued

Dimer Interface Interactions in Obligate Heterodimers of FokI Nuclease Domain Variants

| Redesign of FokI Dimer Interface Residues | Amino Acid Changes or Replacements Chain (A) | Chain (B) | H-bond Interactions (A) | (B) | H-bond Interactions (A) | (B) | H-bond Interactions (A) | (B) | Hydrophobic Interactions (A) | (B) |
|---|---|---|---|---|---|---|---|---|---|---|
| RELV_DKAK (PBPL/JHU)[4] | 483-Arg (R) 486-Glu (E) 499-Leu (L) 538-Val (V) | 487-Asp (D) 490-Lys (K) 499-Ala (A) 538-Lys (K) | R487-D483 (Bi-dentate) (2.7/2.7 A°) | | R483-G480 (Single H-bond) (3.5 A°) | | E486-K490 (Single H-bond) (3.3 A°) | | — | |

[1]Wah et al (1998);
[2]Miller et al (2007);
[3]Szczepek et al (2007) and
[4]PBPL/JHU (this example)

FACS and Microscopy Analyses

HEK293 cells carrying a mutated eGFP reporter gene were transiently transfected with a donor plasmid carrying a fragment of wild-type GFP and plasmids expressing various 3- and 4-finger CCR5-specific ZFN constructs using Lipofectamine 2000 are described in references 21 and 27. Transfections of various obligate heterodimer variants and FokI_WT were performed one after another on the same day. After each transfection, the treated cells were split into 2 flasks. GFP positive cells in about 10,000 treated cells in each flask were determined by FACS and then normalized to one million treated cells. The difference between the two independent FACS readings is shown as error bars. Three, five and seven days post-transfection with ZFNs and donor plasmid, eGFP gene correction was measured by FACS using a BD FACS Canto II. GFP fluorescence (GFP) was measured using BP 530/30 filter. BD FACS Diva™ Software, v6.1.1 was used for analyses. GFP positive cells were sorted and examined by microscopy to confirm GFP expression. Independent transfections, performed using 3-finger ZFN variant pairs on different days, showed a similar trend for gene correction efficiencies of EL_KK and REL_DKK, respectively.

Western Blot Analysis of Obligate Heterodimer Variants Expression in HEK293 Flp-In Cells Western blot analysis was performed are described in reference 32. HEK293 Flp-In cells were grown and transfected are described in reference 21. After 30 hours cells were harvested and resuspended in RIPA buffer (Sigma-Aldrich). 50 µg of total protein of cell extract were separated by 10% SDS-PAGE and transferred to PVDF membrane (Amersham Biosciences). The blot was blocked and incubated with a rabbit anti-FokI antibody (1:200) followed by incubation with horseradish peroxidase-conjugated secondary antibody (Amersham Biosciences, 1:1000) and developed using an ECL chemiluminescence detection system (Thermo Scientific) according to manufacture's instructions. The expression levels (band intensities) of Fok_WT (171.82), RV_DA (171.54), EL_KK (169.51) and REL_DKK (169.05), respectively, were quantified using the Image J software NIH, Version 1.36b).

Analysis of Genome-Wide Double-Strand Breaks in ZFN-Treated Cells

For cytotoxicity analysis, cells were transfected with 400 ng each of ZFN expression plasmid using Lipofactamine 2000 (Invitrogen) according to manufacture's instructions. Alternatively, cells were exposed to 10 µM etoposide for 60 minutes 2 h before harvesting. Cells were collected 30 h after transfection and fixed in ice-cold methanol for 15 min at room temperature, permeabilized in 0.5% Triton X-100 and then blocked using 5% serum for 45 minutes at room temperature. After blocking, cells were then incubated with anti-53BP1 rabbit polyclonal antibodies (Bethyl Laboratories) overnight at 4° C. followed by incubation with AlexaFluor 594-conjugated secondary antibodies (Invitrogen-Molecular Probes) with 2 µg/ml of DAPI (Roche) at room temperature in the dark for one hour. Slides were mounted and analyzed by fluorescence microscope.

Results

Miller et al (2007) strategy for obligate heterodimer development comprised of two key elements: First, ensure that the FokI nuclease domain variants retained the desired catalytic activity by using the functional screen of GFP reporter gene correction in human cells (32). Second, use a stepwise approach to modification of the dimer interface using rational design. This was done through four cycles of variant design and testing, each of which substituted one amino acid at the dimer interface providing incremental improvement in the specificity of heterodimer formation. In each cycle of development, a small panel of amino acid substitutions was generated within one cleavage domain, while its partner was not modified. The choice of substitution was guided by the co-ordinates of the native crystal structure of FokI restriction endonuclease dimer and mutations were introduced at positions that could contact the unmodified partner with a bias towards charge-charge interactions. Each variant was screened for the ability to stimulate gene correction in two different configurations, namely as a heterodimer with the unmodified partner and as a homodimer, alternating successive development cycles between the two sides of the dimer interface. In each cycle of development, they were able to identify a variant that was efficiently induced gene correction as heterodimer, but showed reduced activity as a homodimer. Through these stringent tests, Sangamo group generated FokI cleavage domain pair with the double mutations, namely Q486E:I499L (FIG. 10, SEQ ID NO: 19) and E490K:I538K (FIG. 11, SEQ ID NO: 21) (also known as EL_KK) that promote obligate heterodimer formation. EL_KK pair was shown to possess ~10-fold reduced cytotoxicity as compared to FokI_WT cleavage domains.

Szczepek et al (2007) also used rational design based on the crystal structure of the native FokI endonuclease and protein modeling to identify critical residues involved in the dimerization of ZFNs (33). FokI endonuclease structure has shown that the dimerization is mainly mediated by helices α4 (residues 479-490 through a pair of salt bridge formation between residues D483/R487) and α5 (residues 528-539) of the cleavage domain, which is also supported by functional data (36, 37). The model also predicted the existence of another contact between Q486 and E490. Thus, the FokI crystal structure indicated that an asymmetric dimer interface could be created by rational redesign by swapping a critical pair of interacting residues, like D483R or R487D. By incorporating similarly charged residues D483/D487 or R483/R487 in the same FokI nuclease domain subunit, one could make formation homodimers unlikely, owing to electrostatic repulsion. Similarly, the residues Q486 and E490 were redesigned to generate variants EE (Q486E) and QK (E490K) that favor heterodimerization over homodimerization. Cathomen lab generated a FokI cleavage domain pair with the double mutations, namely D483R:I538V (FIG. 9, SEQ ID NO: 17) and R487D:I499A (FIG. 8, SEQ ID NO: 15) (also known as RV_DA) that promote obligate heterodimer formation. RV_DA pair was shown to possess reduced cytotoxicity as compared to FokI_WT cleavage domains. Later, DD_RR pair was also shown to have reduced cytotoxicity (34).

Engineering of Improved Obligate Heterodimer Variants of FokI Cleavage Domain

The following example makes further improvements to the obligate heterodimer variants of FokI cleavage domain, to further minimize off-target cleavage and lower ZFN toxicity, and thereby increase the efficacy and efficiency of ZFN-mediated gene targeting of human cells. Such mutants also greatly increase the viability of gene-modified human cells, especially the sensitive human primary cells, human embryonic stem cells (hESC) and human induced pluripotent stem cells (hiPSC). Here, we used two different approaches to improve the obligate heterodimer variants of FokI cleavage domain for creating designed ZFNs with minimal toxicity.

We generated two pairs of new obligate heterodimer variants of FokI cleavage domain with lowered ZFN toxicity. The monomer of one of the sets contained the mutations, D483R: Q486E:I499L (FIG. 1, SEQ ID NO: 1), while its dimer partner contained the mutations, R487D:E490K:I538K (FIG. 2, SEQ ID NO: 3). Together the pair is depicted as REL_DKK. The second pair contained one more mutant residue in each of monomer chains in addition to the above: D483R:Q486E: I499L:I538V (FIG. 3, SEQ ID NO: 5) and R487D:E490K: I499A:I538K (FIG. 4, SEQ ID NO: 7). Together the pair is depicted as RELV_DKAK.

In a second approach, we replaced the FokI segment (IVDTKAYSGGYNLPIGQADEMQRYVEENQTRNKHI NPNEWWKVYPSSVTEFKFLFVSGHFKGNYKAQLTR LNHITN (SEQ ID NO: 23)) (see FIG. 12, SEQ ID NO: 23) containing the α4 and α5 helices (in italics and shaded yellow) that mediate dimerization between two monomers of the FokI cleavage domains with the corresponding segment from StsI, an isoschizomer of FokI endonuclease.

The segment in each of the monomer was replaced with LDSKAYSEGFPLTASHTRAMERYLRQFTERKEELKPT WWDIAPEHLDNTYFAYVSGSSFSGNYKEQLQKFRQ DT (SEQ ID NO: 68) (see FIG. 10, SEQ ID NO: 19) and ILDSKAYSEGFPLTASHTDAMGDYLKQFTERKEEIKP TWWDIAPEHLDNTYFAYVSGSFSGNYKEQLQKFRQK T (SEQ ID NO: 69) (see FIG. 11, SEQ ID NO: 21) respectively, to further decrease the affinity at the dimer interface. Furthermore, based on our results from the first approach, we also replaced three amino acid residues within the StsI segment of each monomer chain (which are shown in bold type and double-underlined) to promote obligate heterodimer formation. Together the pair is referred to as FokI_StsI. Since many of the amino acid residues of the StsI segment are quite distinct from the residues within the FokI segment, we reasoned that this would result in further destabilization of the dimer interface and decrease the formation of homodimers, while promoting the heterodimers.

Protein modeling and energy minimization of the obligate heterodimer variant pairs of FokI cleavage domain, EL_KK, RV_DA, REL_DKK and RELV_DKAK respectively, were carried out using the SPDBV software (described in detail in the supplementary material). Visualization of protein structure rendering of images for H-bond interactions were performed with CCP4 MG software. The H-bond interactions that were present between the A and B monomer chains of the different obligate heterodimer variants are shown in FIG. 13. For the REL_DKK pair, the model revealed only one bidentate H-bond between residues R487 of chain A and the D483 of chain B, predicting the weakest dimer interface interactions between the two monomers.

Figure 14:
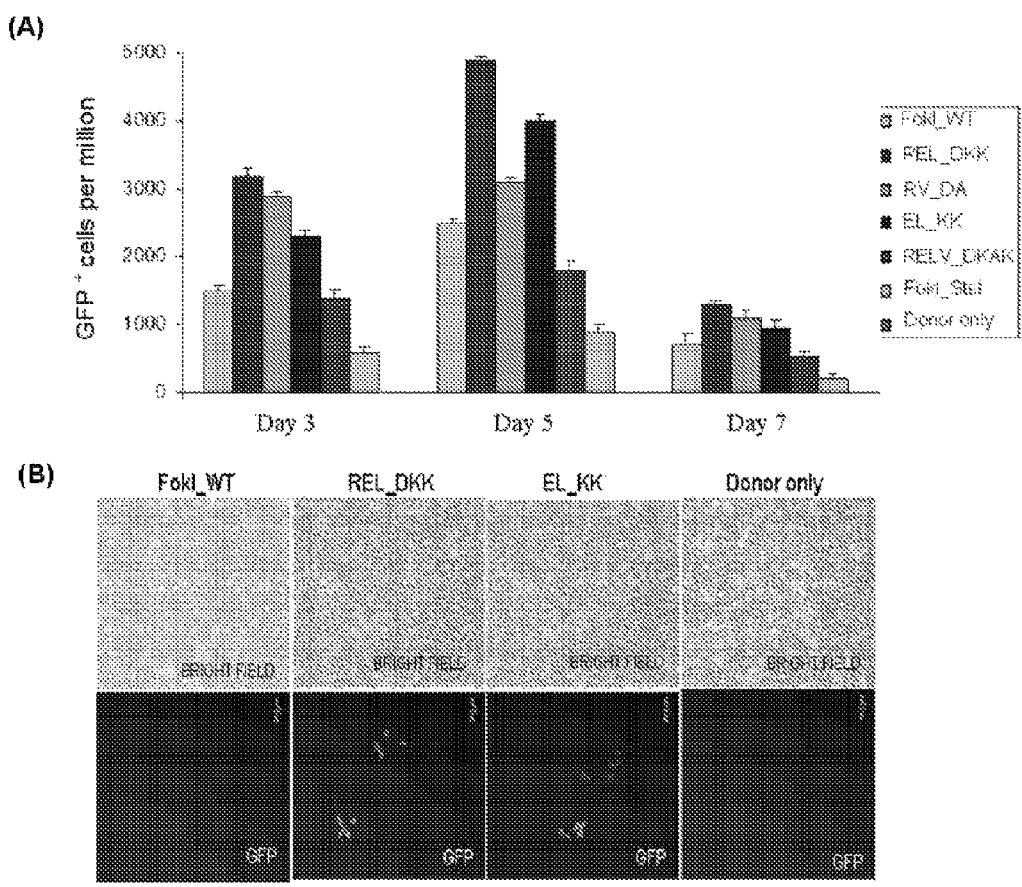
FIG. 14 shows the efficiency and efficacy of CCR5 3- and 4-finger ZFNs (generated by fusing the corresponding ZFPs to various obligate heterodimer variants of FokI nuclease domain) using the GFP gene targeting reporter system. HEK293 cells carrying a mutated eGFP reporter gene were transiently transfected with a donor plasmid carrying a fragment of wild-type GFP and plasmids expressing various 3- or 4-finger CCR5-specific ZFN constructs, using Lipofectamine 2000 as described elsewhere (21,27). Transfections of various obligate heterodimer variants and FokI_WT were performed one after another on the same day. After each transfection, the treated cells were split into 2 flasks. GFP positive cells in about 10,000 treated cells in each flask were determined by FACS and then normalized to one million treated cells. The difference between the two independent FACS readings is shown as error bars. A) Frequency of gene correction in HEK293 Flp-In cells of a chromosomal mutant GFP reporter disabled by insertion of the CCR5 ZFN target sequences using 4-finger ZFNs (28, 29). Quantitative FACS analyses of the GFP positive cells at 3, 5 and 7 days post-transfection with designer CCR5-specific 4-finger ZFNs (constructs carrying the FokI_WT and obligate heterodimer FokI nuclease domain variants) and donor plasmids. WT: wild type; EL_KK, 4-finger CCR5-ZFNs containing the FokI nuclease domain mutants reported by Miller et al., 2007 (32). RV_DA, 4-finger CCR5-ZFN constructs carrying the FokI nuclease domain mutants reported by Szczepek et al., 2007 (33). REL_DKK, RELV_DKAK and FokI_StsI, 4-finger CCR5-ZFN constructs carrying the FokI nuclease domain mutants that were generated at PBPL/JHU. B) Top panel: HEK293 Flp-In cells 5 days post-transfection as seen in brightfield; Bottom panel: GFP positive cells as seen 5 days post-transfection of HEK293 Flp-In cells with 3-finger CCR5-ZFN constructs (carrying Fok_WT, EL_KK or REL_DKK respectively) and donor plasmid. No GFP positive cells were seen with either donor alone or ZFNs containing FokI_WT nuclease domains and donor plasmid. C) FACS analyses of the frequency of gene correction in HEK293 Flp-In cells using 3-finger CCR5 ZFN constructs carrying FokI_WT, EL_KK, REL_DKK or donor alone, respectively. Results from two independent transfections, performed on different days, are shown in Figure S1; both transfections showed a similar trend of gene correction efficiencies for EL_KK and REL_DKK, respectively. The dose response curve using titrations of 3-finger ZFN expression plasmids, EL_KK and REL_DKK respectively, at constant donor plasmid, are shown in FIG. 17. D) Analysis of the genotype of nine different individual GFP positive clones. Five days post-transfection with CCR53-finger ZFNs and the donor plasmids, GFP positive cells were sorted, serially diluted to get individual clones and grown. The genomic DNA was isolated from the GFP positive clones and the eGFP gene at the Flp-In locus was PCR amplified and digested with BstXI. The mutant eGFP gene has two BstXI sites, where the ZFN binding sites are inserted. Correction of the eGFP gene by homology-directed repair results in the loss of the BstXI sites. The PCR product size of the corrected eGFP gene is 930 bp as compared to 990 bp for the mutant gene. BstXI digestion of the mutant eGFP PCR product generates two bands: 450 bp and 540 bp, respectively. Lanes: Control, PCR product of the mutant eGFP gene from untransfected cells before (−) and after (+) digestion with BstXI; GFP$^+$1-9, PCR products of 9 different individual clones obtained from GFP positive sorted cells before (−) and after (+) digestion with BstXI; M, 1 Kb ladder. All GFP positive cells are resistant to BstXI digestion, confirming ZFN-mediated eGFP gene correction in these cells.

Testing the Efficacy and Efficiency of Engineered Obligate Heterodimer FokI Nuclease Domain Variants Using the Proxy GFP Gene Targeting Reporter System in HEK293 Cells We compared the efficiency and efficacy of gene targeting of the various pairs of obligate heterodimer variants (REL_DKK; RELV_DKAK and FokI_StsI) with those of FokI_WT, EL_KK pair from Sangamo and RV_DA pair from Cathoman lab, by making fusions to the previously published pair of 4-finger ZFPs that was shown to target CCR5 in human cells (28,29). ZFN-mediated gene correction at the mutant GFP locus was very efficient in HEK293 Flp-In cells, yielding GFP positive cells upon transduction with the corresponding pairs of ZFNs containing either FokI_WT or the obligate heterodimer variants (FIG. 14). Transfection with donor alone did not yield any GFP positive cells by microscopy. Quantitative FACS analyses of the GFP positive cells at 3, 5 and 7 days post-transfection with designer various ZFN pairs and donor plasmids are shown in FIG. 14A. The number of surviving GFP positive cells using the REL_DKK mutant pair at 3, 5 and 7 days post-transfection was consistently better in gene targeting experiments as compared to the other obligate heterodimer variant pairs, therefore that they are less toxic to cells, due to reduced off-target cleavage.

Figure 15:
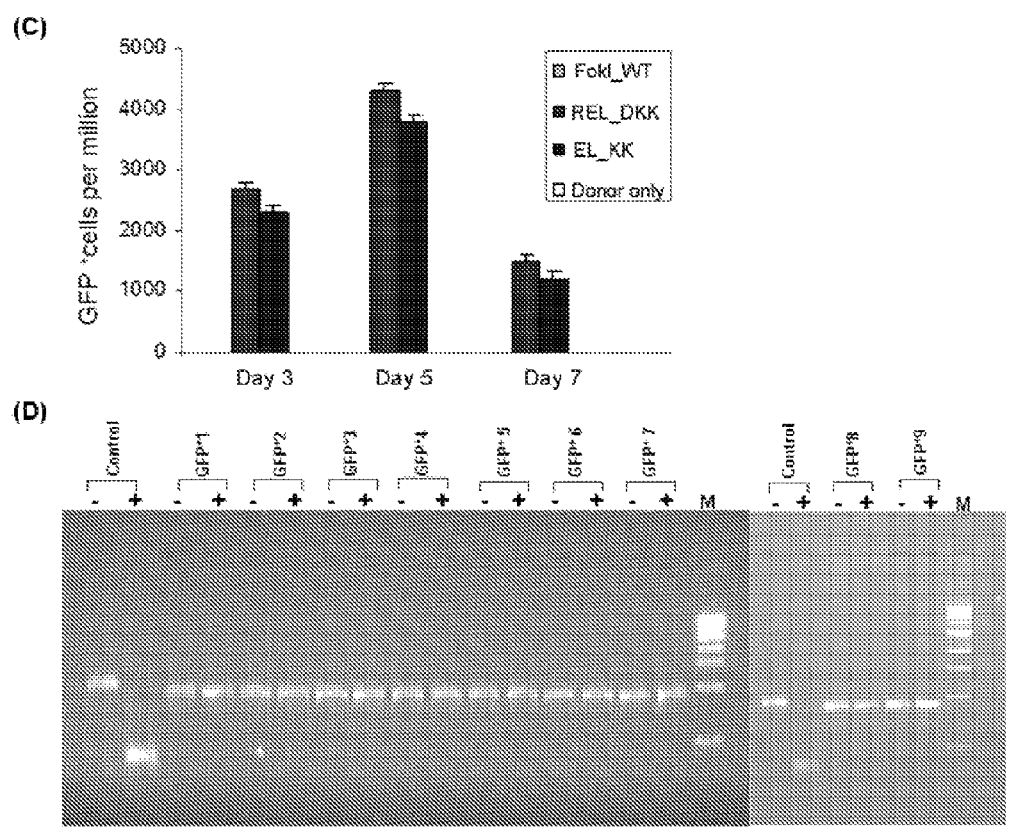
FIG. 15 shows genotypic analysis of the endogenous CCR5 locus at the 3- and 4-finger ZFN target sites of the GFP+ clones *The complete 3- and 4-finger ZFN target sites present in hCCR5 gene are highlighted in yellow and blue, respectively, in WT sequences. $^#$PCR fragments amplified from each of the GFP+ clones were subcloned into *E. coli*. Four clones from each subcloning experiment were sequenced. The number of times the same sequence appeared is shown in brackets. WT denotes wild type. Insertions are shown in bold lowercase letters. Dots denote deletions. ˆ, Homozygous mutations.

Once established, the gene-altered cells are viable and they continued to increase in number for several weeks. We isolated 3 different individual GFP positive clones from gene targeting experiment REL_DKK mutant pair by serial dilution of FACS sorted GFP positive cells and grew them for genotypic characterization. Three different loci, namely the mutant GFP locus, the endogenous CCR5 locus and the CCR2 locus, were PCR-amplified using the corresponding locus-specific primers from the isolated genomic DNA of the individual GFP positive clones. The PCR DNA from the mutant GFP locus of the gene-altered clones were all resistant to BstXI digestion indicating that gene correction to the wild-type sequence has occurred in the GFP positive clones. The PCR DNA from the three different loci was then cloned in the pGEMT vector for transformation into E. coli. DNA sequence analysis of at least 4 recombinant E. coli clones from each individual GFP positive clone confirmed that gene correction indeed has occurred. DNA sequence analysis of 4 recombinant bacterial clones generated by cloning the PCR-amplified DNA of the endogenous CCR5 locus from each of the three individual GFP positive clones, as expected, showed simple deletion and/or insertion mutations at the targeted 4-finger CCR5 site resulting from NHEJ (FIG. 15). Extensive genotypic characterization of the GFP positive cells from gene targeting experiments using 4-finger CCR5-specific ZFNs is described in reference 21.

Figure 16:
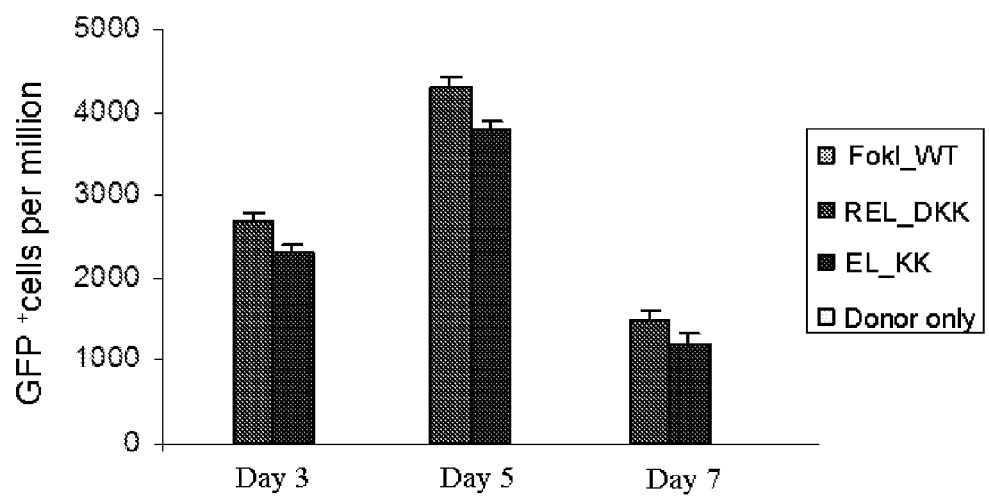
FIG. 16 show two independent transfections to confirm the efficiency and efficacy of 3-finger ZFNs (generated by fusing the corresponding ZFPs to EL_KK and REL_DKK variants of FokI nuclease domain, respectively) using the GFP gene targeting reporter system. HEK293 cells carrying a mutated eGFP reporter gene were transiently transfected with a donor plasmid carrying a fragment of wild-type GFP and the plasmids expressing 3-finger CCR5-specific ZFN constructs using Lipofectamine 2000 as described in FIG. 14. For each independent transfection experiment (A & B respectively), the co-transfections of EL_KK and REL_DKK variants were performed one after another on the same day. After each co-transfection, the treated cells were split into 2 flasks. GFP positive cells in about 10,000 treated cells in each flask were determined by FACS and then normalized to one million treated cells. The difference between the two independent FACS readings is shown as error bars. Independent transfection experiment shown in FIG. 14C is included as part of this figure.
Figure 16:
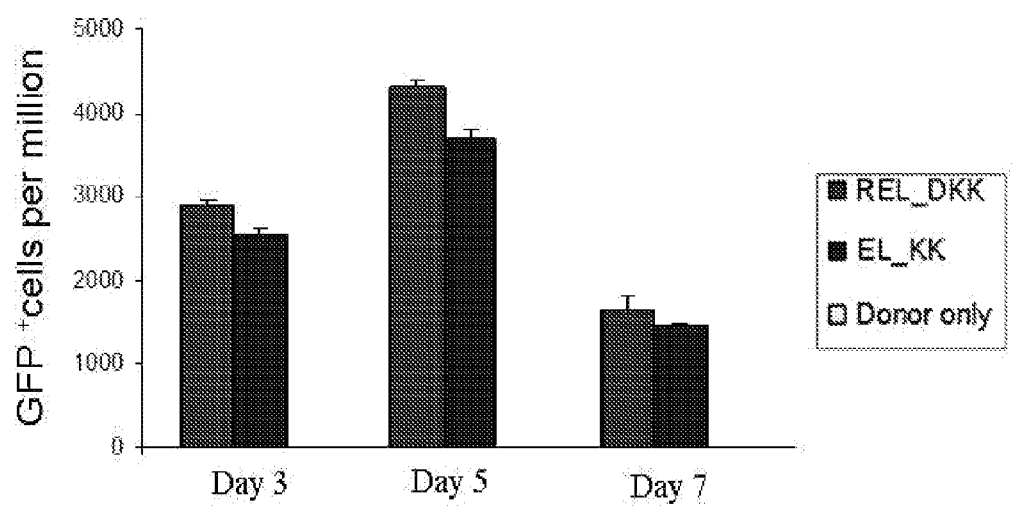
Figure 17:
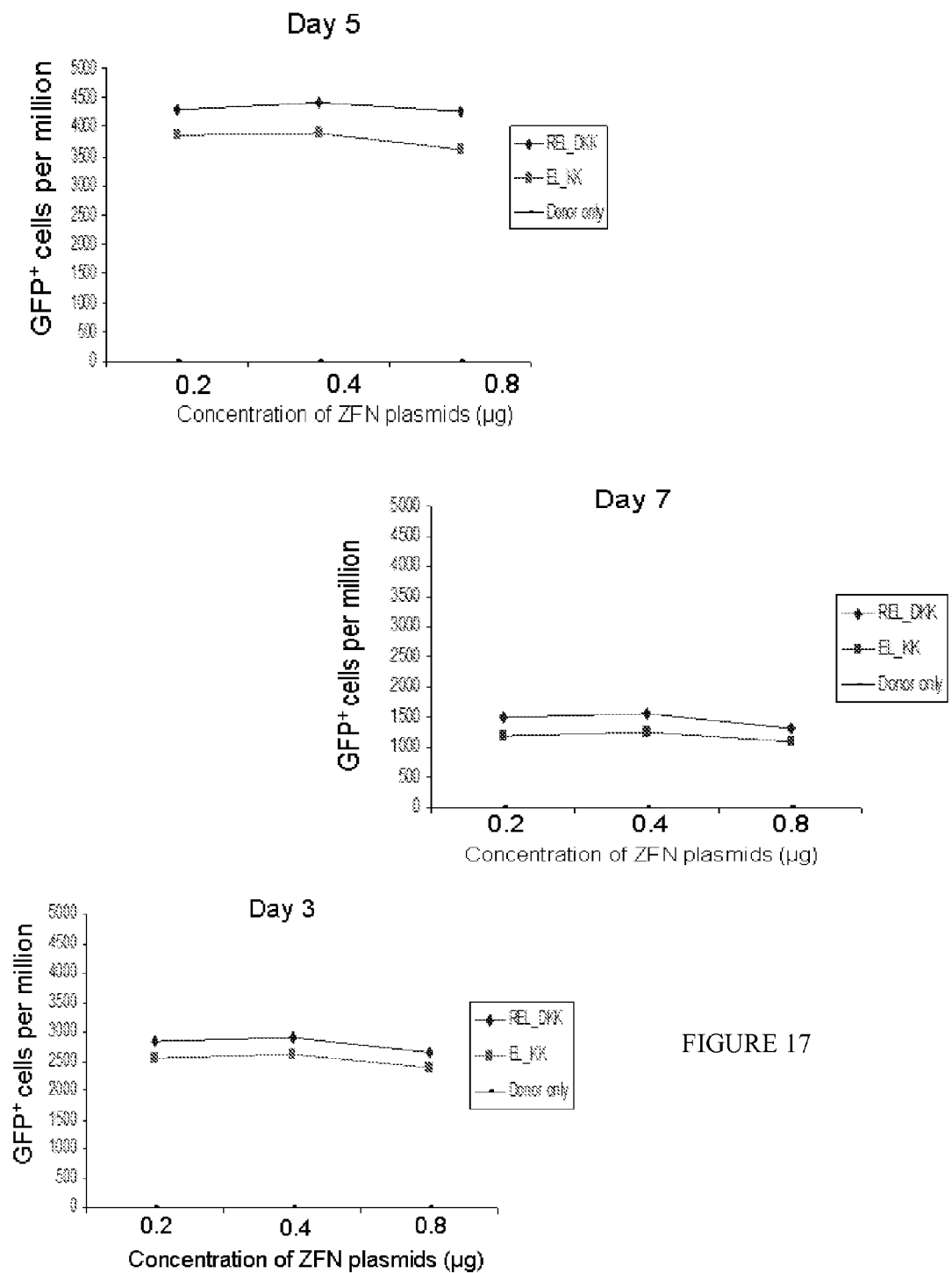
FIG. 17 shows a dose response curve using titrations of 3-finger ZFN expression plasmids, EL_KK and REL_DKK, respectively. The dose response curve was obtained by independent co-transfection of varying concentrations (200, 400 and 800 ng respectively) of 3-finger ZFN expression plasmids at constant donor plasmid concentration (1 µg). FACS analysis was performed at 3, 5 and 7 days post-transfection as discussed in FIG. 14 and in FIG. 16.

We then compared the efficiency and efficacy of gene targeting of REL_DKK obligate heterodimer variant pair with those of FokI_WT and EL_KK pair from Sangamo by making fusions to the 3-finger ZFPs that target CCR5 in human cells (13). Unlike the CCR54-finger ZFNs which had no linker, the active CCR5-specific 3-finger ZFNs contained the $(Gly_4S)_3$ linker between the ZFPs and the FokI nuclease domain variants, since they are designed to target ZFN sites separated by a 12 bp spacer (13). Transfection with donor alone or ZFPs fused to FokI_WT and donor did not yield any GFP positive cells by microscopy (FIG. 14B). ZFN-mediated gene correction at the mutant GFP locus was very efficient in HEK293 Flp-In cells, upon transfection with 3-finger ZFPs fused to REL_DKK or EL_KK obligate heterodimer FokI nuclease domain mutants and donor, yielding GFP positive cells (FIG. 14B). Quantitative FACS analyses of the GFP positive cells at 3, 5 and 7 days post-transfection are shown in FIG. 14C. The GFP positive cells using the REL_DKK mutant pair at 3, 5 and 7 days post-transfection was consistently higher in gene targeting experiments as compared to EL_KK pair, suggesting that REL_DKK variants are less toxic to cells, which is likely due to further reduction in off-target cleavage. Results from two independent transfections, performed on different days, are shown in FIG. 16; both transfections showed a similar trend for gene correction efficiencies of EL_KK and REL_DKK, respectively. We also performed titrations of 3-finger ZFN expression plasmids of obligate heterodimer variants EL_KK and REL_DKK at 0.2, 0.4 and 0.8 µg respectively, with constant donor plasmid (1.0 µg) to obtain a dose response curve to study the differences between the two mutants (FIG. 17). REL_DKK variant consistently yielded more gene corrected cells as compared to EL_KK mutant. The maximal difference of GFP corrected cells was observed 5 days post co-transfection of plasmids (FIG. 17).

Once established, the gene-corrected cells are viable and they continued to increase in number for several weeks. We isolated 9 different individual GFP positive clones from gene targeting experiment using REL_DKK mutant pair by serial dilution of FACS sorted GFP positive cells and grew them for genotypic characterization. Three different loci, namely the mutant GFP locus, the endogenous CCR5 locus and the CCR2 locus, were PCR-amplified using the corresponding locus-specific primers from the isolated genomic DNA of the individual GFP positive clones. The PCR DNA from the mutant GFP locus of the gene-altered clones were all resistant to BstXI digestion indicating that gene correction to the wild-type sequence has occurred in the GFP positive clones (FIG. 14D). The PCR DNA from the three different loci was then cloned in the pGEMT vector for transformation into *E. coli*. DNA sequence analysis of at least 4 recombinant *E. coli* clones from each individual GFP positive clone confirmed that gene correction indeed has occurred. DNA sequence analysis of 4 recombinant bacterial clones generated by cloning the PCR-amplified DNA of the endogenous CCR5 locus from each of the individual GFP positive clones, as expected, showed simple deletion and/or insertion mutations at the targeted 3-finger CCR5 site resulting from NHEJ (FIG. 15). No change in the nucleotide sequence of the CCR2 locus was observed in the limited number of GFP positive clones that were sequenced suggesting that the designed pair of 3-finger CCR5ZFNs did not cleave at a distantly related site (data not shown).

Reduced Levels of DNA Damage by REL_DKK Heterodimer Variant Pair

Figure 18:
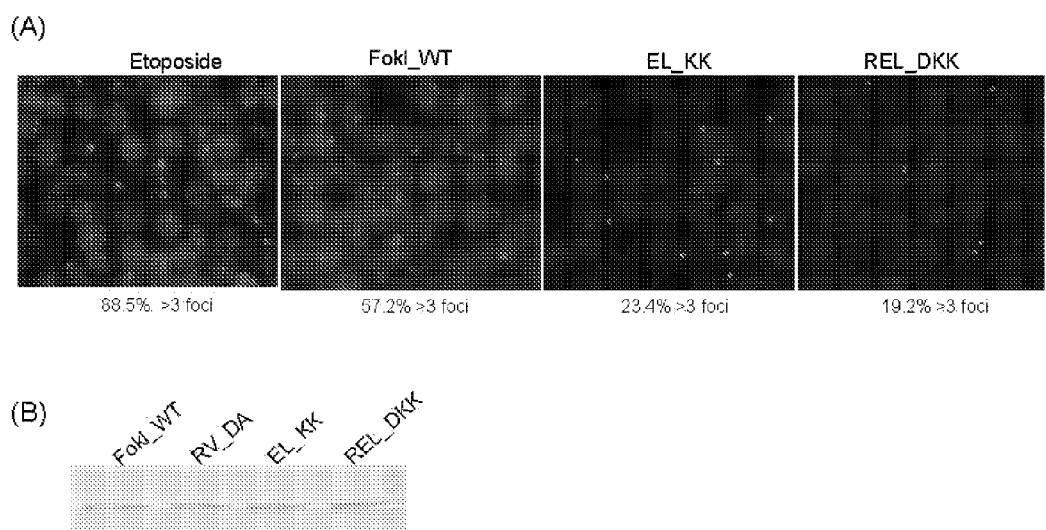
FIG. 18 shows the reduced genome-wide DNA damage levels by REL_DKK obligate heterodimer variant pair of FokI nuclease domain. A), Representative images of cells treated with the DNA cleavage agent etoposide or transfected with the indicated ZFN expression plasmids. Cells were fixed after 30 h and stained with antibodies against 53BP1 (red) and then with DAPI (blue). The fraction of cells containing more than 3 foci is indicated under each panel. The total number of cells analyzed is: etoposide, 152; FokI_WT, 245; EL_KK, 282; REL_DKK, 289. B), ZFN expression levels were examined by anti-FokI immunoblot analysis. HEK293 Flp-In cells were transfected with indicated ZFN expression plasmids and cells were harvested after 30 h. Equal amounts of total cellular protein was separated by 10% SDS-PAGE gel and transferred to PVDF membrane. The blot was probed with anti-FokI antibody. The ZFNs migrate as a single band on the gel. Western blot analysis shows comparable levels ZFN expression for various obligate heterodimer variants in HEK293 Flp-In cells.

As a direct measurement for ZFNs' cytotoxicity, we then monitored whether REL_DKK heterodimer variant pair reduced genome-wide DNA cleavage levels when expressed in human HEK293 Flp-In cells using the well-established assay for visualizing DNA double-strand breaks as described in reference 32. We used antibody-mediated detection of the protein 53BP1, which localizes to sites of DNA damage and forms foci that are visualized by immunofluoroscence. Antibody-based detection of 53BP1 revealed that substitution of either EL_KK or REL_KK heterodimer variant pair for FokI_WT cleavage domain showed marked reduction in the number of 53BP1-stained foci in HEK293 Flp-In cells (FIG. 18A). Moreover, the fraction of 53BP1-stained cells with multiple foci (>3 foci) for REL_DKK heterodimer variants was lower than that of EL-KK variants (FIG. 18A). We confirmed that the observed results were not due to poor protein expressions of REL_DKK variants in HEK293 Flp-In cells, since western blot analysis showed comparable levels of ZFN expressions for FokI_WT, EL_KK and REL_DKK, respectively (FIG. 18B).

Discussion

This example details further improvements to obligate heterodimer variants, by incorporating multiple mutations at the dimer interface of FokI cleavage domains, to eliminate or greatly reduce ZFN toxicity, while increasing the efficacy and efficiency of ZFN-mediated gene targeting in cells. Our results indicate that the REL-DKK pair fused to 3- and 4-finger ZFPs consistently performed better as compared to EL_KK or RV_DA, suggesting this pair exhibits the lowest toxicity to human cells, while retaining catalytic efficiency of the FokI_WT cleavage domains.

Using 3D protein modeling based on FokI crystal structure and energy minimization calculations, we analyzed the H-bond and hydrophobic interactions present at the dimer interface of the newly generated mutant pairs. The RELV_D-KAK model predicts the existence of one additional H-bond interaction including those that are present in REL_DKK pair, which likely provides added stability to the dimer interface. The FokI_StsI pair generated by replacing the FokI segment (encoding the α4 and α5 helices that are involved in the dimer interface interactions) with the StsI segment in FokI nuclease domain, although active, appears to have much diminished catalytic activity, which is probably due to the destabilizing effect of the StsI segment on protein folding of the FokI nuclease domains.

While the 4-finger CCR5ZFNs (created by fusing highly specific 4-finger ZFPs to FokI_WT cleavage domains) were efficient in GFP gene correction assays, the 3-finger CCR5-specific ZFNs (created by fusing modular 3-finger ZFPs to FokI_WT cleavage domains) did not yield any GFP positive cells, suggesting that sequence-specificity of the designed ZFNs is the major determinant of ZFN activity for efficient gene targeting and for greatly reduced cellular toxicity. The toxicity resulting from off-target cleavage could be attributed to: (i) Homodimer formation by the individual ZFN species; and (ii) Relaxed specificity of the ZF modules (used to generate ZFPs by modular assembly), which results in degenerate or off-target binding by ZFNs (10). However, when the corresponding CCR5-specific ZFPs were fused to the obligate heterodimer variants of FokI nuclease domains, the ZFNs were active in the GFP gene targeting reporter system indicating that the off-target cleavage could be eliminated or greatly reduced by fusing 3-finger ZFPs to obligate heterodimer variant pair (REL_DKK).

Our results from GFP gene correction experiments are consistent with the mechanism of double-strand cleavage by natural FokI enzyme (36-39) and by ZFNs (7). Bitinaite et al (1998) reported that although FokI enzyme binds DNA as a monomer, dimerization of the nuclease domains is required to form active sites in order to cleave DNA (36, 37). Later studies have shown that an active dimer could form with just one subunit bound to its recognition site, albeit through a weak protein-protein interaction of the nuclease domains, particularly at high enzyme concentrations (38). Studies on the mechanism of cleavage by ZFNs suggest that binding of two ZFN monomers to two binding sites is required for effective double-strand DNA cleavage (7). We speculate that ZFN monomers bound to a single site are unlikely to form an active dimer by associating with another ZFN monomer that is not bound to DNA, since this has to occur through the weak protein-protein interaction. It is more likely that the off-target cleavage results, when one ZFN monomer is bound to its cognate site while the other is bound to a nearby degenerate site (since all ZF modules do not always contact all the three bases within their cognate triplets, which could result in relaxed specificities) or bound non-specifically to DNA, especially at high protein concentrations. Interactions at the dimer interface could provide additional stability to the off-target cleavage site complexes, inducing DSB at these sites, resulting in ZFNs' toxicity to human cells. In such instances, destabilization of the dimer interface would greatly diminish ZFNs off-target cleavage, leading to lowered toxicity to cells. Our results lend support to this idea.

ZFN technology applications in human therapeutics depend on the ability to create custom-designed ZFNs that cleave the target sequences with exquisite sequence-specificity and high affinity (27). Highly specific ZFPs fused to the re-engineered obligate heterodimer variant pair (like REL_DKK described in this example) will be critical for eliminating or greatly reducing ZFN toxicity to human cells. This will allow one to deliver a targeted genomic DSB to human cells, while leaving the rest of the genome unchanged. Such engineered highly specific ZFNs will enable wider application of ZFN technology in human therapeutics, by further increasing the viability of the gene-modified cells, especially the sensitive human primary cells, human embryonic stem cells (hESC) and human induced pluripotent stem cells (hiPSC).

References cited herein are listed below for convenience and are hereby incorporated by reference in their entirety.

(1) Kim, Y-G., Cha, J., and Chandrasegaran, S. (1996) *Proc. Natl. Acad. Sci. USA.* 93, 1156-1160
(2) Li, L., Wu, L. P., and Chandrasegaran, S. (1992). *Proc. Natl. Acad. Sci. USA.* 89, 4275-4279
(3) Lin, L. and Chandrasegaran, S. (1993) *Proc. Natl. Acad. Sci. USA.* 90, 2764-2768
(4) Kim, Y-G., and Chandrasegaran, S. (1994). *Proc. Natl. Acad. Sci. USA.* 91, 883-887
(5) Bibikova, M., Carroll, D., Segal, D. J., Trautman, J. K., Smith, J., Kim, Y-G. and Chandrasegaran, S. (2001) *Mol Cell Biol.* 21, 289-297
(6) Smith, J., Bibikova, M., Whitby, F. G., Reddy, A. R., Chandrasegaran, S, and Carroll, D. (2000) *Nucleic Acids Res.* 28, 3361-3369
(7) Mani, M., Smith, J., Kandavelou, K., Berg, J. M. and Chandrasegaran, S. (2005) *Biochem Biophyl Res Commun.* 334, 1191-1197
(8) Wu, J., Kandavelou, K. and Chandrasegaran, S. (2007) *Cellular and Molecular Life Sciences.* 64, 2933-2944
(9) Kandavelou, K., Mani, M., Durai, S, and Chandrasegaran, S. (2005) *Nat. Biotechnol.* 23, 686-687
(10) Durai, S., Mani, M., Kandavelou, K., Wu, J., Porteus, M. and Chandrasegaran, S. (2005) *Nucleic Acids Research.* 33, 5978-5990
(11) Durai, S., Bosley, A., Abulencia, A. B., Chandrasegaran, S, and Ostermeier, M. (2006) Journal of Combinatorial Chemistry & High Throughput Screening. 9, 301-311
(12) Maeder, M. L., Thibodeau-Beganny, S., Osiak, A., Wright, D. A., Anthony, R. M., Eichtinger, M., Jiang, T., Foley, J. E., Winfrey, R. J., Townsend, J. A. et al. (2008) *Mol. Cell.* 31, 294-301
(13) Mani, M., Kandavelou, K., Dy, J. F., Durai S, and Chandrasegaran S. (2005) *Biochem Biophys Res Commun.* 335, 447-457
(14) Beumer, K., Bhattacharyya, G., Bibikova, M., Trautman, J. K. and Carroll, D. (2006) *Genetics.* 172, 2391-2403
(15) Bibikova, M., Beumer, K., Trautman, J. K. and Carroll, D. (2003) *Science.* 300, 764
(16) Bibikova, M., Golic, M., Golic, K. G. and Carroll, D. (2002) *Genetics.* 161, 1169-1175
(17) Morton, J., Davis, M. W., Jorgensen, E. M. and Carroll, D. (2006) *Proc Natl Acad. Sci. USA.* 103, 16370-16375
(18) Meng, X., Noyes, M. B., Zhu, L. J., Lawson, N. D. and Wolfe, S. A. (2008) *Nat. Biotechnol.* 26, 695-701
(19) Doyon, Y., McCammon, J. M., Miller, J. C., Faraji, F., Ngo, C., Katibah, G. E., Amora, R., Hocking, T. D., Zhang, L., Rebar, E. J. et al. (2008) *Nat. Biotechnol.* 26, 702-708
(20) Foley, J. E., Yeh, J. R., Maeder, M. L., Reyon, D., Sander, J. D., Peterson, R. T. and Joung, J. K. (2009) *PLoS ONE.* 4, e4348
(21) Kandavelou, K., Ramalingam, S., London, V., Mani, M., Wu, J., Alexeev, V., Civin, C. I. and Chandrasegaran S. (2009). *Biochem BiophyRes Commun.* 388, 56-61
(22) Geurts, A. M., Cost, G. J., Freyvert, Y., Zeitler, B., Miller, J. C., et al. (2009) *Science.* 325, 433
(23) Mashimo, T., Takizawa, A., Voigt, B., Yoshimi, K., Hiai, H., Kuramoto, T., and Serikawa, T. (2010) *PLoS ONE.* 5, e8870
(24) Townsend, J. A., Wright, D. A., Winfrey, R. J., Fu, F., Maeder, M. L., Joung, J. K. and Voytas, D. F. (2009) *Nature.* 459, 442-445
(25) Shukla, V. K., Doyon, Y., Miller, J. C., DeKelver, R. C., Moehle, E. A., Worden, S. E., Mitchell, J. C., Arnold, N. L., Gopalan, S., Meng, X. et al. (2009) *Nature.* 459, 437-441
(26) Porteus, M. H. and Baltimore, D. (2003) *Science.* 300, 763
(27) Urnov, F. D., Miller, J. C., Lee, Y. L., Beausejour, C. M., Rock, J. M., Augustus, S., Jamieson, A. C., Porteus, M. H., Gregory, P. D. and Holmes, M. C. (2005) *Nature.* 435, 646-651
(28) Lombardo, A., Genovese, P., Beausejour, C. M., Colleoni, S., Lee, Y. L., Kim, K. A., Ando, D., Urnov, F. D., Galli, C., Gregory, P. D. et al. (2007) *Nat Biotechnol* 25, 1298-1306
(29) Perez, E. E., Wang, J., Miller, J. C., Jouvenot, Y., Kim, K. A., Liu, O., Wang, N., Lee, G., Bartsevich, V. V., Lee, Y. L. et al. (2008) *Nat. Biotechnol.* 26, 808-816
(30) Hockemeyer, D., Soldner, F., Beard, C., Gao, Q., Mitalipova, M., DeKelver, R. C., Katibah, G. E., Amora, R., Boydston, E. A., Zeitler, B. et al. (2009) *Nat Biotechnol* 27, 851-857
(31) Kim, H. J., Lee, H. J., Kim, H., Cho, S. W. and Kim, J. S. (2009) *Genome Res.* 19, 1279-1288

(32) Miller, J. C., Holmes, M. C., Wang, J., Guschin, D. Y., Lee, Y. L., et al, (2007) *Nat. Biotechnol.* 25, 778-785

(33) Szczepek, M., Brondani, V., Buchel, J., Serrano, L., Segal, D. J. and Cathomen, T. (2007) *Nat Biotechnol,* 25, 786-793

(34) Pruett-Miller, S. M., Connelly, J. P., Maeder, M. L., Joung, J. K. and Porteus, M. H. (2008) *Molecular Therapy,* 16, 707-717.

(35) Pruett-Miller, S. M., Reading, D. W., Porter, S. N. and Porteus, M. H. (2009) *PLoS Genet.* 5, e1000376

(36) Wah, D. A., Hirsch, J. A., Dorner, L. F., Schildkraut, I. and Aggarwal, A. K. (1998) *Proc. Natl. Acad. Sci. USA.* 95, 10564-10569.

(37) Bitinaite, J., Wah, D. A., Aggarwal, A. A. and Schildkraut, I. (1998) *Proc. Natl. Acad. Sci. USA.* 95, 10570-10575

(38) Vanamee, E. S., Santagata, S, and Aggarwal, A. K. (2001) *J. Mol. Biol.* 309, 69-78

(39) Catto, L. E., Ganguly, S., Milsom, S. E., Welsh, A. J. and Halford, S. E. (2006) *Nucleic Acids Research.* 34, 1711-1720

(40) Miller et al., A TALE nuclease architecture for efficient genome editing, Nat. Biotechnol. 2011 February; 29(2): 143-8. Epub 2010 Dec. 22.

(41) Hockemeyer et al., Genetic engineering of human pluripotent cells using TALE nucleases, Nat. Biotechnol. 2011 Jul. 7. doi: 10.1038/nbt.1927.

We claim:

1. A polypeptide comprising either a first engineered FokI cleavage domain variant D483R:Q486E:I499L (SEQ ID NO: 1), or a second engineered FokI cleavage domain variant R487D:E490K:I538K (SEQ ID NO: 3), the first engineered FokI cleavage domain variant forming an obligate heterodimer with the second engineered FokI cleavage domain variant.

2. The polypeptide of claim 1, wherein the obligate heterodimer comprises a first monomer containing the polypeptide designated D483R:Q486E:I499L (SEQ ID NO: 1), and a second monomer containing the polypeptide designated R487D:E490K:I538K (SEQ ID NO: 3).

3. The polypeptide of claim 1, further comprising a DNA-binding domain.

4. The polypeptide of claim 3, wherein the DNA-binding domain comprises zinc finger protein (ZFP) domain or transcription activator-like effector (TALE) domain.

5. A polynucleotide encoding the polypeptide of the claim 1.

6. An isolated cell or cell line comprising the polypeptide or a polynucleotide encoding the polypeptide of the claim 1.

* * * * *